United States Patent [19]

Baker et al.

[11] 4,121,917

[45] Oct. 24, 1978

[54] ETHYLENE PRODUCTION WITH UTILIZATION OF LNG REFRIGERATION

[75] Inventors: Charles Richard Baker; Harry Cheung, both of Kenmore, N.Y.

[73] Assignee: Union Carbide Corporation, New York, N.Y.

[21] Appl. No.: 730,290

[22] Filed: Oct. 6, 1976

Related U.S. Application Data

[63] Continuation-in-part of Ser. No. 611,704, Sep. 9, 1975, abandoned.

[51] Int. Cl.² .................................................. F25J 3/02
[52] U.S. Cl. ............................................ 62/28; 62/23; 62/40; 62/41; 62/52
[58] Field of Search .................... 62/23, 28, 40, 41, 52

[56] References Cited

U.S. PATENT DOCUMENTS

| 2,777,305 | 1/1957 | Davison | 62/28 |
|---|---|---|---|
| 3,367,122 | 2/1968 | Tutton | 62/28 |
| 3,398,545 | 8/1968 | Nelson et al. | 62/40 |
| 3,398,546 | 8/1968 | Nelson et al. | 62/40 |
| 3,405,530 | 10/1968 | Donahan et al. | 62/28 |
| 3,479,832 | 11/1969 | Sarsten et al. | 62/40 |
| 3,524,897 | 8/1970 | Kniel | 62/40 |
| 3,635,038 | 1/1972 | Nagel et al. | 62/23 |
| 3,849,096 | 11/1974 | Kniel | 62/23 |

FOREIGN PATENT DOCUMENTS 1,011,518 12/1965 United Kingdom.

OTHER PUBLICATIONS

Kniel, L., "LNG Cold Potential Could Cut Ethylene Costs", *The Oil Gas Journal*, Sep. 15, 1969, pp. 96–99.

*Primary Examiner*—Norman Yudkoff
*Attorney, Agent, or Firm*—Steven J. Hultquist

[57] ABSTRACT

A process for utilizing liquefied natural gas as a source of refrigeration in an ethylene plant of the type featuring a "front-end" depropanizer and a forecooling recovery section, wherein the forecooling section is operated at lower than conventional temperature and pressure levels while the final separation section is maintained at conventional operating conditions. Liquefied natural gas is heat exchanged with recovered depropanizer column overhead gas in the forecooling section and with overhead of the demethanizer and $C_2$ splitter columns to condense reflux, thereby closely matching the cooling curve of the ethylene plant with the LNG warming curve to achieve highly efficient utilization of the LNG refrigeration.

20 Claims, 12 Drawing Figures

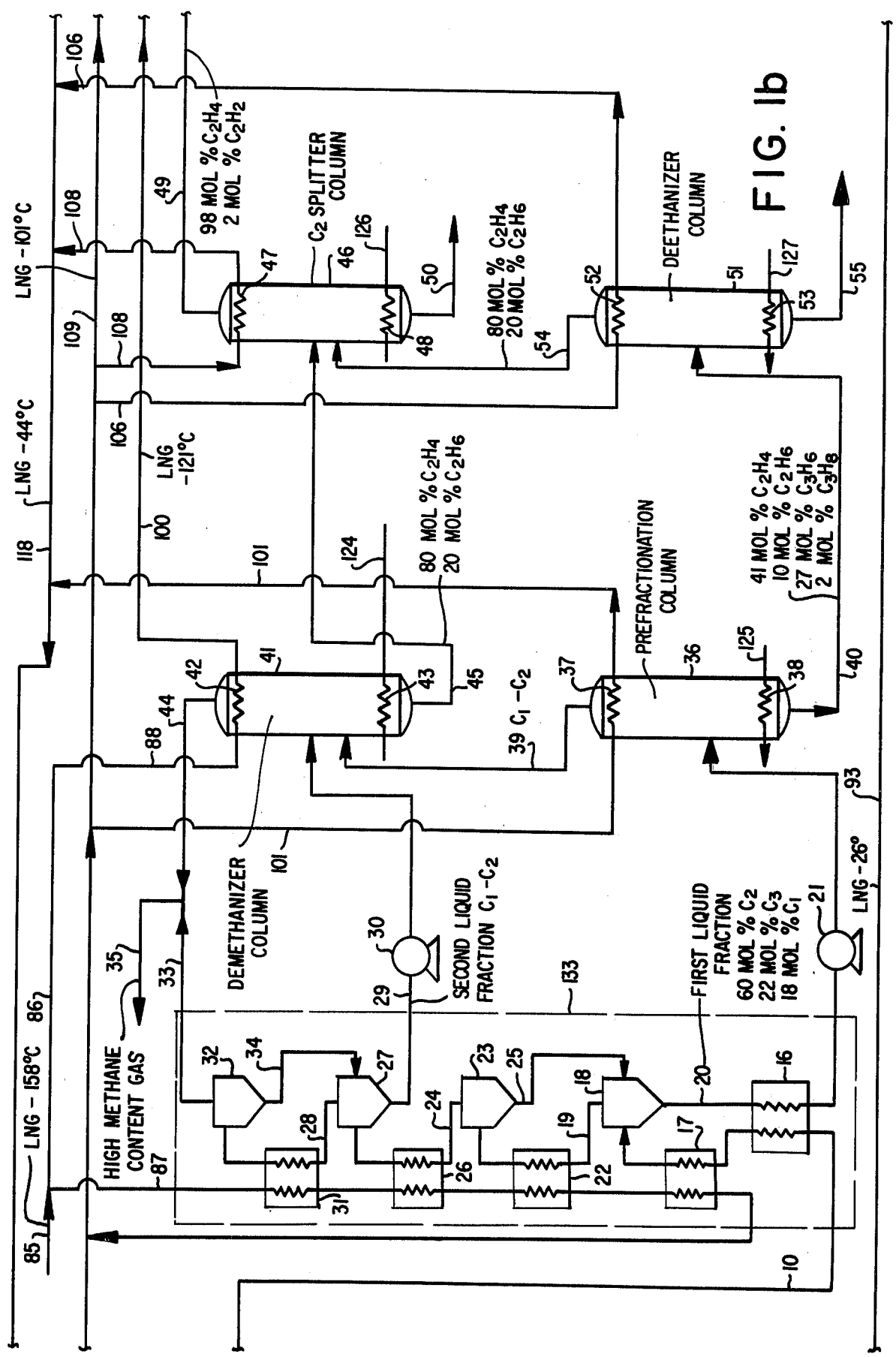

ETHYLENE PRODUCTION WITH UTILIZATION OF LNG REFRIGERATION

CROSS-REFERENCE TO RELATED APPLICATION

This application is a continuation-in-part of U.S. Ser. No. 611,704 filed Sept. 9, 1975, now abandoned.

BACKGROUND OF THE INVENTION

This invention relates generally to a method for using liquefied natural gas as a source of refrigeration in a process for separating a hydrocarbon feed gas mixture to produce a separated ethylene product.

Liquefaction is commonly employed to facilitate transportation of natural gas where great distances separate the source and distribution points. Liquefaction offers the advantage of greatly reducing the volume of the natural gas, e.g., by a factor of roughly 600 at a pressure of one atmosphere. Removal of substantial amounts of sensible and latent heat is required for liquefaction, however; at one atmosphere, for example, natural gas liquefies at approximately $-160°$ C. There is thus considerable "cold" stored in the liquefied natural gas (LNG). Since the ultimate use of natural gas is characteristically at ambient or near ambient temperatures, the LNG is generally revaporized at the point of distribution. With such vaporization, there is opportunity to employ the refrigeration associated with the "cold" and thereby recover work initially expended on the natural gas to liquefy it.

There have been many attempts by the prior art to use the refrigeration associated with LNG by integrating LNG vaporization with a variety of commercial processes, for example, air separation, hydrogen recovery from refinery tail gases, liquefaction of trans-shipment "cold carriers", and olefins (ethylene) production. In particular, much work has been done on integrating LNG revaporization with ethylene plants, since the latter characteristically employ in-plant refrigeration at temperature levels from $0°$ C. down to $-100°$ C. and lower.

In conventional ethylene plants, the low temperature fractionation steps for separating the various components of the olefin-containing hydrocarbon feed stream are typically conducted at relatively high pressures of 400–600 psig, with refrigeration for the separation steps being supplied by propylene at temperature levels down to about $-40°$ C. and by ethylene at levels down to about $-100°$ C. This refrigeration system, although efficient, is expensive due to the provision of large and costly refrigeration compressors.

In some ethylene plants, methane refrigeration has been employed in conjunction with propylene and ethylene refrigerants in cascaded refrigeration systems. Such cascaded systems permit temperatures as low as $-130°$ C. to be achieved and allow the operating pressures of the fractionation steps to be substantially reduced, for example to 150–200 psig, by virtue of the lower temperatures. Triple-cascaded systems, however, require additional methane refrigeration compressors, and the savings in feed stream compression is not large enough to provide an overall practical advantage for the cascaded system. As a result, methane refrigeration has not been used widely in commercial ethylene plants.

It has been recognized, however, that the process gains which result from the use of methane refrigeration in ethylene production can be realized without penalty by the use of liquefied natural gas (LNG) as a refrigerant, in locations where natural gas distribution networks or use facilities exist in close proximity to the ethylene plant. An efficient utilization of LNG allows the in-plant (propylene-ethylene) refrigeration system to be eliminated or, at the very least, substantially reduced, with corresponding elimination or reduction of the investment and operating costs for the refrigeration compressors. Additionally, the lower temperatures characteristic of LNG permit a reduction in the operating pressures of the fractionation equipment, so that the investment and operating costs for the feed gas compression system are likewise reduced.

Regarding the fractionation steps of the ethylene plant in greater detail, two general process equipment sequences are widely employed. One sequence incoporates a demethanizer column at the head end of the fractionation section followed by de-ethanizer and $C_2$ splitter columns, depropanizer and $C_3$ splitter columns, debutanizer column, depentanizer column, and other separation equipment as required. This is perhaps the most generally employed arrangement; however, it has been established that significant process gains are realized in many cases by positioning the depropanizer at the head of the fractionation section, so that $C_3$'s and lighter are separated from $C_4$'s and heavier initially. The so-called front-end depropanizer scheme permits better maintenance of olefin (ethylene) purity specifications, and substantially reduces capital, power, and operating costs over a front end demethanizer arrangement. By removing the $C_4$'s and heavier initially, the subsequent separation equipment can operate at extremely low temperatures without the problems arising from freezing of heavy hydrocarbon components. Operation at such extremely low temperatures allows particularly efficient light component separations. In one especially preferred arrangement for a front-end depropanizer system, the light components in the depropanizer overhead stream are separated and removed in a forecooling recovery section, with the remaining olefin-bearing streams passing to the final separation section. This arrangement, with the forecooling recovery section operating at low temperature, is particularly suitable in connection with the use of LNG as a source of refrigeration.

The efficiency of LNG-supplied refrigeration in any ethylene plant is related to how closely the LNG enthalpy/temperature warming curve is able to approach the corresponding cooling curve for the olefins plant. The "match" between these two curves will determine how well the LNG provides the refrigeration requirements for the plant. There are, however, certain practical considerations which apply to this match. For example, it is desirable to avoid temperature "pinches" (excessively small $\Delta T$'s) in the process heat exchangers between the cooling and warming streams. Such pinches require prohibitively large amounts of heat transfer area to achieve the desired heat transfer. In addition, it is necessary to avoid very large temperature differences, since energy losses in heat exchangers are dependent on the temperature differences of the heat exchanging fluids. Large energy losses are in turn associated with heat exchange irreversibilities or inefficiencies which waste the LNG refrigeration potential.

The prior art, in order to achieve reasonable process efficiencies under the above considerations, has deliberately kept process integrations of LNG vaporization and ethylene production simple in nature and limited in scope. Such restrictions minimize the number of refrigeration loads on the warming LNG and thereby permit a readily accomplished matching of LNG to system refrigeration requirements with moderate efficiency. The prior art has not, however, been able to efficiently employ LNG refrigeration in a complex ethylene facility having a front end depropanizer coupled with an extensive fore-cooling recovery section and final separation section. In prior art integrations, the fractionation of olefin-bearing feed gas has been carried out either at high (>200 psig) pressures to provide reasonable matches between the supplied LNG and the system refrigeration requirements or else, when good matching is obtained, at low (>200 psig) pressures, to take advantage of savings from reduced feed gas compression requirements. Neither of these approaches is completely desirable to the above-described ethylene plant having a front-end depropanizer and forecooling section. At high pressures, the overall investment and operating savings for the implementation of LNG refrigeration in this plant yield a modest economic advantage but the effectiveness of the supplied refrigeration is low. At low pressures, there exist imbalances in the refrigeration requirements over the various temperature ranges which would result in highly inefficient overall LNG utilization.

Accordingly, it is an object of the present invention to provide an improved process integration of ethylene production with LNG warming for regasification thereof.

It is a further object of the invention to implement LNG refrigeration in an ethylene plant of the type employing a front-end depropanizer and forecooling recovery section in a highly efficient manner.

It is a still further object of the invention to provide an implementation of LNG refrigeration in an ethylene plant which is characterized by higher levels of LNG refrigeration utilization and effectiveness than are achieved by the integration schemes of the prior art.

Other objects and advantages of this invention will be apparent from the ensuing disclosure and appended claims.

SUMMARY OF THE INVENTION

This invention relates to a process for separating a hydrocarbon feed gas mixture comprising at least $C_1-C_4$ constituents including ethylene to produce a separated ethylene product while simultaneously warming liquefied natural gas for refrigeration thereof.

In the method of the invention, the hydrocarbon feed gas mixture is provided at superatmospheric pressure and fractionated in a depropanizer column to recover overhead gas comprising $C_3$ and lighter constituents and bottoms comprising $C_4$ and heavier constituents. The overhead gas recovered from the depropanizer column is cooled to condense a liquid fraction comprising at least $C_1-C_2$ constituents by heat exchange with externally supplied liquefied natural gas for warming thereof, and the liquid fraction is separated from the cooled overhead gas. The separated liquid fraction is pressurized to a superatmospheric pressure higher than the pressure of the feed gas mixture, and then fractionated in a demethanizer column to recover a demethanizer overhead comprising methane and a demethanizer bottoms comprising at least $C_2$ constituents. Externally supplied liquefied natural gas is heat exchanged with the demethanizer overhead to condense same and provide reflux for the demethanizer while warming the liquefied natural gas. The demethanizer bottoms is further fractionated for the production of the separated ethylene product. This further fractionating includes fractionation in a $C_2$ splitter column to recover ethylene as overhead product and ethane bottoms. Externally supplied liquefied natural gas is heat exchanged with the $C_2$ splitter column overhead to condense same and provide reflux for the $C_2$ splitter column while warming the liquefied natural gas.

In the above-described process of this invention, the further fractionation of the demethanizer bottoms may be carried out in several distinct ways. For example, the demethanizer bottoms may be directly fractionated in the $C_2$ splitter column to produce ethylene as overhead product from the column. In such arrangement, it may also be desirable to sequentially cool the overhead gas recovered from the depropanizer column, so as to condense and separate two liquid fractions. The second lower temperature condensed liquid fraction is then pressurized and passed to the demethanizer column as described above, while the first higher temperature condensed liquid fraction has been separated after the initial cooling thereof, to condense a second liquid fraction. Such second liquid fraction is then pressurized in a manner similar to the second condensed liquid fraction and employed as feed for prefractionation or deethanization steps in connection with the previously described demethanizing and $C_2$ splitting operations. In another arrangement, the further fractionation of the demethanizer bottoms may be carried out by fractionating the demethanizer bottoms in a deethanizer column to recover a $C_2$ overhead and a $C_3$ bottoms, with the recovered $C_2$ overhead then being fractionated in the $C_2$ splitter column to produce ethylene as overhead product.

In a preferred embodiment of the invention, the hydrocarbon feed gas mixture is provided at a first superatmospheric pressure and fractionated in a depropanizer column to recover overhead gas comprising $C_3$ and lighter constituents and bottoms comprising $C_4$ and heavier constituents. The overhead gas recovered from the depropanizer column is cooled to condense a first liquid fraction comprising $C_1-C_3$ constituents by heat exchange with externally supplied liquefied natural gas for warming thereof, and the first liquid fraction is separated from the cooled overhead gas. The first liquid fraction is pressurized to a second higher-than-first superatmospheric pressure and then fractionated in a prefractionation column to recover a prefractionated overhead comprising $C_2$ and lighter constituents and a prefractionated bottoms comprising $C_2-C_3$ constituents. Further cooling of the uncondensed overhead gas from the first liquid fraction condensing step is conducted to condense a second liquid fraction comprising $C_1-C_2$ constituents by heat exchange with externally supplied liquefied natural gas for warming thereof, followed by separation of the second liquid fraction from the further cooled gas. The second liquid fraction is then pressurized to a third higher-than-first super-atmospheric pressure and fractionated along with the prefractionated overhead recovered from the prefractionation column in a demethanizer column to recover a demethanizer overhead comprising methane and a demethanizer bottoms comprising $C_2$ constituents. Externally supplied liquefied natural gas is heat exchanged with the demethanizer overhead to condense same and provide reflux for the demethanizer while warming the liquefied natural gas. Prefractionated bottoms recovered from the prefractionation column are fractionated in a deethanizer column to recover a C₂ overhead and C₃ bottoms. The C₂ overhead and the demethanizer bottoms are fractionated in a C₂ splitter column to recover ethylene as overhead product and ethane bottoms, and externally supplied liquefied natural gas is heat exchanged with the C₂ splitter column overhead to condense same and provide reflux for the C₂ splitter column while warming the liquefied natural gas.

In one particularly advantageous embodiment under the method of the present invention, liquefied natural gas is further employed as a source of refrigeration in a low temperature scrubbing complex wherein ethylene overhead product from the C₂ splitter column containing acetylene is treated to remove substantially all acetylene therefrom. Ethylene overhead product and externally supplied acetone are contacted in an absorber column and acetylene is absorbed in the acetone therein to recover overhead final product of substantially pure ethylene and bottoms liquid comprising acetone and acetylene. Bottoms liquid recovered from the absorber column is cooled by heat exchange with externally supplied liquefied natural gas for warming thereof. The cooled absorber column bottoms liquid is fractionated in a first fractionation column to recover overhead containing a lower fraction of acetylene and bottoms containing a higher fraction of acetylene. Externally supplied liquefied natural gas is heat exchanged with the first fractionation column overhead to condense same and provide reflux for the first fractionation column while warming the liquefied natural gas, and the first fractionation column overhead is returned to the absorber column as recycle therefor. The first fractionation column bottoms is fractionated in a second fractionation column to recover acetone bottoms and overhead containing acetylene.

Externally supplied liquefied natural gas is heat exchanged with acetone bottoms recovered from the second fractionation column for cooling thereof while warming the liquefied natural gas, and the cooled acetone bottoms is returned to the absorber column as the acetone feed therefor. Acetylene-containing overhead gas recovered from the second fractionation column is then cooled to condense substantially all acetone therein by heat exchange with externally supplied liquefied natural gas for warming thereof. Condensate is separated from the cooled overhead and returned to the second fractionation column as recycle therefor, and the cooled overhead gas is discharged as substantially pure acetylene.

In still another preferred embodiment of the invention, the ethylene production process employs deethanizer and C₃ splitter columns, the hydrocarbon feed gas mixture contains propylene and the deethanizer bottoms is fractionated in the C₃ splitter column to recover propylene as overhead product, the ratio of the total flow rate of liquefied natural gas heat exchanged in the ethylene production process as refrigerant in standard cubic feet per day to the rate of production of olefins (taken here as meaning product ethylene and product propylene) by the process in lbs./year is between 0.05 and 0.30, the superatmospheric pressure of the feed gas mixture is less than 150 psig and the superatmospheric pressure of the liquid condensed from the overhead gas recovered from the depropanizer column and pressurized is greater than 250 psig. Such conditions insure a particularly high level of LNG refrigeration effectiveness.

As used herein the term "recover" or "recovered stream" will be understood to relate to an overhead or bottoms stream which is discharged from a given separation column subsequent to the associated respective reflux condensing or reboil vaporizing operations. The terms "gas" and "gaseous" will be understood to refer to both gases and vapors.

BRIEF DESCRIPTION OF THE DRAWINGS

FIGS. 1a, 1b, and 1c are contiguous sections of a schematic flowsheet of an ethylene plant employing LNG as a source of refrigeration according to one embodiment of the invention.

DESCRIPTION OF THE PREFERRED EMBODIMENTS

Figure 1A:
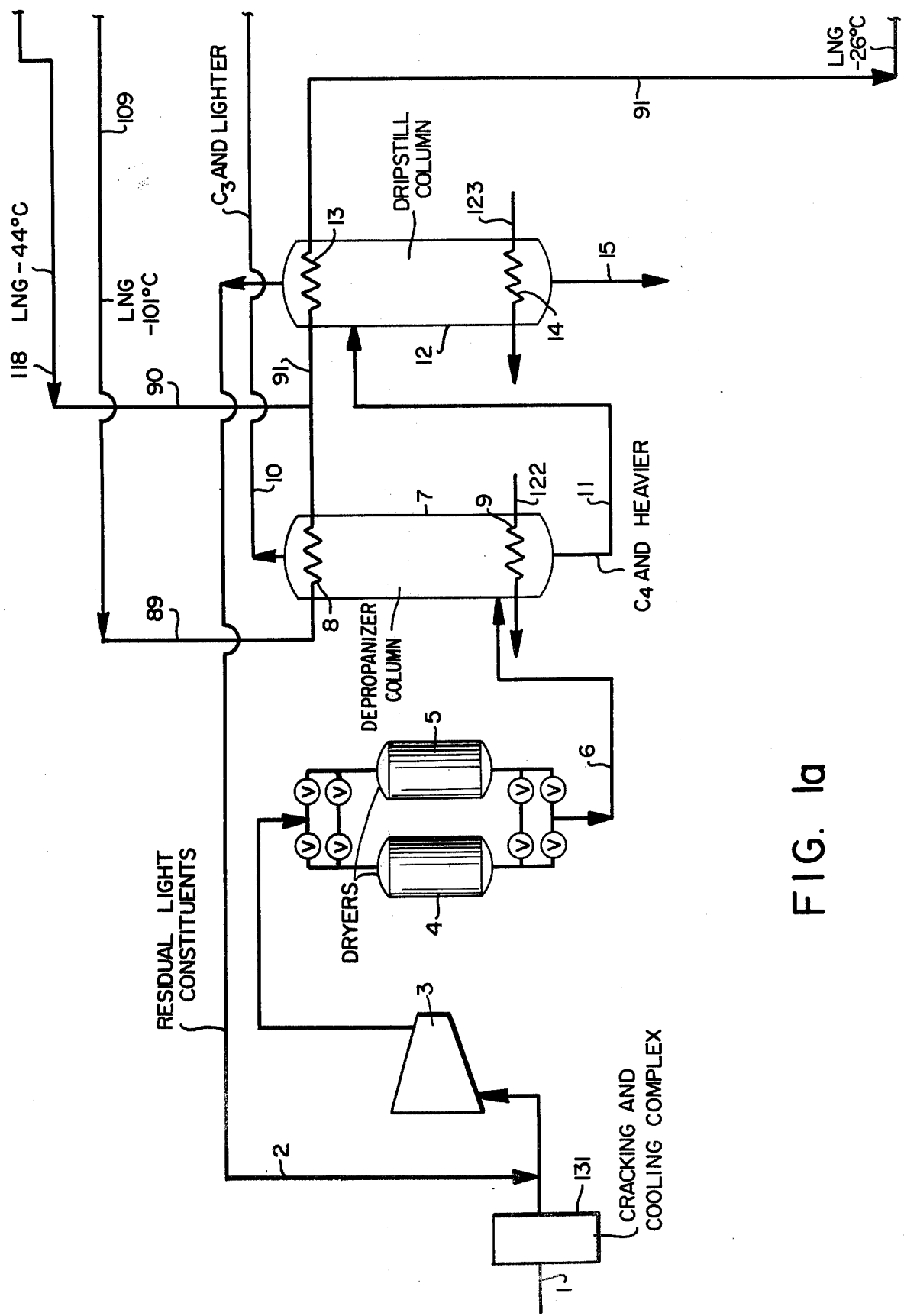

Referring now to the drawings, FIG. 1 shows an illustrative schematic flowsheet of an ethylene plant employing LNG as a source of refrigeration according to one embodiment of the invention. The following description of FIG. 1 will be based on a naphtha feed mixture having the following approximate composition by volume: paraffins — 76%, olefins — 0.3%, naphthenes — 17.7% and aromatics — 6%. The LNG refrigerant employed in the illustrative plant is suitably pressurized to approximately 700 psig prior to its introduction to the process, thereby permitting discharge of the ultimately revaporized natural gas to a gas distribution pipeline at pressure sufficiently high to obviate gas compression while matching the available refrigeration temperature levels of the LNG to the requirements of the ethylene plant.

The ethylene plant shown in FIG. 1 employs an equipment sequence featuring a front-end depropanizer, forecooling recovery section and final separation section. The naphtha feed mixture enters the process through line 1 and passes into the treatment complex 131 for cracking and cooling therein in a manner well known to those skilled in the art. Cracking is generally carried out in high temperature furnaces wherein endothermic pyrolysis and dehydrogenation reactions occur to yield an olefin-rich hydrocarbon gas mixture. The effluent hot gases from the cracking furnace are thereafter rapidly quenched with boiler feed water to prevent further reaction, thereby generating high pressure steam which is used to drive the various compressors in the ethylene plant. After quenching, the cracked gas is further cooled to remove water (deriving from steam added to the naphtha upstream of the cracking furnace to depress polymerization and heavy residue formation therein) and the heaviest hydrocarbons, and is then joined with the recycle stream 2 (to be described more fully hereinafter), and sent to the compressor 3. The compressor is suitably of the steam turbine-driven centrifugal type comprising three individual stages of compression with intercooling and condensate removal after each stage wherein the cracked gas is compressed to approximately 125 psig. Compressed gas from the final compression stage is then dried in one of the two fixed-bed, desiccantfilled dryers 4 and 5 suitably manifolded in parallel flow relationship for alternate sequential operation in a well-known manner.

The dried cracked gas discharged from the desiccant bed, as for example comprising the following approximate molar composition: hydrogen — 10%, methane — 26%, ethylene — 26%, ethane — 6.5%, acetylene — 0.5%, propylene — 17%, propane — 1%, and the remainder $C_4$ and heavier constituents, is provided as the hydrocarbon feed gas mixture for the process at a pressure of about 125 psig and introduced by line 6 to depropanizer column 7 having overhead reflux condenser 8 and bottoms reboiler 9. In the depropanizer column 7 the cracked hydrocarbon feed gas mixture is fractionated to recover overhead gas comprising $C_3$ and lighter constituents, discharged through line 10, and bottoms comprising $C_4$ and heavier constituents. Reboil heat imput for the depropanizer is supplied by steam entering reboiler 9 in line 122 and reflux is provided by heat exchanging LNG from line 89 in reflux condenser 8 with the depropanizer overhead stream for partial condensing thereof while warming the liquefied natural gas. The bottoms recovered from the depropanizer column is introduced via line 11 to the drip still column 12 for separation therein of the residual $C_3$ and lighter constituents in the depropanizer bottoms. These residual light constituents are recovered as overhead from the drip still and recycled through line 2 to the compressor 3. Drip still overhead is condensed for reflux for the column by heat exchange with LNG flowing through recycle condenser 13 from line 91. Reflux vapor is generated by high pressure, e.g. 200 psig, steam flowing through reboiler 14 from line 123. The bottoms recovered from the drip still column is discharged from the process in line 15 and may be sequentially fractionated in other separation columns (not shown) to yield major heavy product streams.

The flowsheet for processing the $C_3$ and lighter constituent-containing overhead gas recovered from the depropanizer column may be functionally divided into two distinct sections: the forecooling recovery section and the final separation section. In the forecooling recovery section 133 illustratively enclosed by a dashed line in FIG. 1, $C_2$- and $C_3$-containing fractions are recovered and routed to the final separation section and a stream of hydrogen/methane is produced. The final separation section, comprising the columns 36, 41, 46, and 51 as described more fully hereinafter, separates the $C_2$ and $C_3$ fractions from the forecooling section into product streams of methane, ethane, ethylene and propylene.

The overhead gas recovered from the depropanizer column enters the forecooling section in line 10 and is sequentially cooled by indirect heat exchange in heat exchanger 16 with the liquid stream in line 20 to be described hereinafter and in heat exchanger 17 with liquefied natural gas from line 87 to condense a first liquid fraction comprising $C_1$–$C_3$ constituents, while warming the liquefied natural gas. Partially condensed depropanizer column overhead enters phase separator 18 for separation of the first liquid fraction from the cooled overhead gas. The first liquid fraction, containing about 60 mole % $C_2$ constituents and 22 mole % $C_3$ constituents, is discharged from the separator in line 20, flows through the aforementioned heat exchanger 16 and out of the forecooling section to pressurizing pump 21 wherein the pressure of the liquid is raised from about 125 psig to approximately 500 psig. Pressurized liquid from the pump 21, at a temperature of approximately $-5°$ C., then enters the final separation section for fractionation therein in a manner to be described more fully hereinafter.

In the forecooling section the uncondensed overhead gas from phase separator 18 flows through line 19 through the heat exchanger 22 for cooling therein to a temperature of about $-70°$ C. by heat exchange with liquefied natural gas from line 87. Condensate resulting from the cooling in exchanger 22 is removed in phase separator 23 and returned to the first separator 18 by line 25; cooled overhead from phase separator 23 is discharged through line 24, passes through heat exchanger 26 for further cooling therein by heat exchange with liquefied natural gas from line 87 to condense a second liquid fraction comprising $C_1$–$C_2$ constituents, and enters phase separator 27. The second liquid fraction is separated from the further cooled gas in separator 27 and is removed therefrom and discharged from the forecooling section in line 29 having pressurizing pump 30 therein. Pump 30 pressurizes the second liquid fraction to approximately 500 psig prior to its introduction to the final separation section. Further uncondensed gas from the phase separator 27 comprising hydrogen and $C_1$–$C_2$ constituents flows by line 28 through heat exchanger 31 for still further cooling therein by LNG from line 87, to condense part of the $C_1$ and virtually all of the residual $C_2$ constituents. The resulting partially condensed stream, at a temperature of approximately $-130°$ C., enters phase separator 32 wherein condensate is separated for return thereof to phase separator 27 by line 34. Uncondensed gas, comprising approximately 40% hydrogen and the remainder methane is discharged from separator 32 by line 33. As shown the discharged stream may be joined with the gaseous methane demethanizer column overhead in line 44 which is recovered from demethanizer column 41 to form a combined gas stream 35 of high methane content which is suitable for use as fuel gas for the pyrolysis furnaces of the ethylene plant. Alternatively the discharged stream 33 may be further cooled, by either heat exchange with LNG or self-cooling or a combination thereof to recover hydrogen at high purity, as for example 95 mole %. The remaining predominantly methane gas may in such case be joined with the recovered demethanizer overhead stream in the aforedescribed manner for use as fuel gas. Additionally, the various fuel gas and hydrogen streams described above may be further heat exchanged with other refrigerant streams (not shown) in a suitable manner to recover their refrigeration.

In the final separation section, the pressurized first liquid fraction in line 20 is introduced into the prefractionation column 36 and fractionated therein to recover a prefractionated overhead comprising $C_2$ and lighter constituents and a prefractionated bottoms comprising $C_2$-$C_3$ constituents. Reboil heat input for the prefractionation column is provided by steam at 15 psig passing through reboiler 38 in line 125 and reflux is provided by heat exchanging LNG from line 101 in reflux condenser 37 with the prefractionation column overhead for partial condensing thereof. The prefractionated overhead recovered from the prefractionation column, containing mainly $C_1$ and $C_2$ constituents, flows by means of line 39 into the demethanizer column 41 as part of the feed stream therefor. The remainder of the feed to the demethanizer column is supplied by the pressurized second liquid fraction introduced to the column in line 29. Reflux for the demethanizer column is provided by condenser 42 wherein the externally supplied LNG flowing therethrough from line 99 is heat exchanged with the demethanizer overhead to condense same while warming the liquefied natural gas. Bottoms liquid revaporizaton for the demethanizer column is provided by 15 psig steam flowing through reboiler 43 from line 124. The pressurized second liquid fraction and the prefractionated overhead recovered from the prefractionation column are fractionated in the demethanizer column to recover overhead of 95% methane which is discharged in line 44 at a temperature of −100° C. and pressure of approximately 480 psig. This stream may be suitably heat exchanged as discussed hereinearlier to recover its refrigeration. Bottoms liquid from the demethanizer column comprising approximately 80 mole % ethylene and 20 mole % ethane at −6° C. are fed to the $C_2$ splitter column 46 as part of the feed stream therefor. The remainder of the $C_2$ splitter column feed comprises overhead recovered from deethanizer 51. The deethanizer column receives the prefractionated bottoms recovered from prefractionation column 36. This bottoms stream, having a molar composition of 41% ethylene, 10% ethane, 47% propylene and 2% propane at a temperature of 22° C., enters the deethanizer column through line 40 and is fractionated therein to recover a $C_2$ overhead comprising 80 mole % ethylene and 20% ethane at −70° C. and 310 psig which is fed to the $C_2$ splitter column through line 54. Overhead reflux for the deethanizer is provided by heat exchanging the deethanizer overhead with LNG entering condenser 52 in line 106 for condensation of the overhead while warming the liquefied natural gas. Reboil vapor for the deethanizer is generated by steam at 15 psig flowing from line 127 through heat exchanger 53. As a further step, the bottoms recovered from the deethanizer column, as for example comprising about 92 mole % propylene, may be introduced into a $C_3$ splitter column (not shown) for fractionation therein to recover propylene as the overhead product as high purity, such as may be desired to provide a polymer grade product stream.

In the $C_2$ splitter column 46, the recovered demethanizer bottoms and deethanizer overhead are fractionated to recover ethane bottoms comprising 98 mole % ethane at −5° C. and 300 psig which is discharged in line 50 and may be recycled to the pyrolysis furnaces for cracking therein along with the feedstock. The $C_2$ splitter column is provided with reboiler 48 having 15 psig steam flowing therethrough from line 126. Reflux is provided for the $C_2$ splitter column by heat exchanging liquefied natural gas from line 108 in condenser 47 with the $C_2$ splitter column overhead to condense same while warming the liquefied natural gas. Overhead product ethylene is recovered from the $C_2$ splitter column at −28° C. and 285 psig comprising approximately 98 mole % ethylene with the remainder mainly acetylene.

Acetylene is removed from the ethylene overhead product from the $C_2$ splitter column to produce a final product of substantially pure ethylene, suitable for polymerization or chemical synthesis in the acetylene removal complex to be described hereinafter. In typical ethylene plants, including the front-end depropanizer type employed in the present invention, the elimination of acetylene from the process streams may be carried out either by low-temperature scrubbing, as described below, or by hydrogenation on a suitable catalyst, e.g. palladium or alumina, whereon acetylene is reacted with hydrogen to form ethylene. There are advantages and disadvantages associated with both methods, and the choice of one over the other is generally determined by considerations which are specific to the given ethylene plant. The provision of a low-temperature scrubbing complex is not an essential feature of the present invention, but when employed, such a scrubbing system permits still higher utilization of the LNG refrigeration than would otherwise be realized in its absence.

In the acetylene removal complex shown in FIG. 1, as comprising the separation columns 56, 64 and 70, ethylene overhead product recovered from $C_2$ splitter column 46 in line 49 and acetone in line 61 are introduced into absorber column 56 wherein acetylene is absorbed to recover overhead final product of substantially pure ethylene and bottoms liquid comprising acetone and actylene. Overhead reflux for the absorber column is condensed by heat exchanging LNG from line 110 in condenser 57 with the overhead of the absorber column to condense same while warming the liquefied natural gas, and reboil vapor is generated by low pressure (15 psig) steam in line 128 flowing through reboiler 58. The overhead final product recovered from the absorber column is substantially pure ethylene, as for example 99.95 mole % purity, which is discharged from the system in line 59 at approximately −30° C. and 235 psig and may be subsequently passed through heat exchangers (not shown) for refrigeration recovery. The bottoms liquid recovered from the absorber column, comprising roughly 82% acetone, 14% ethylene and 4% acetylene at 45° C. and 265 psig, is discharged in line 60, sequentially cooled in heat exchangers 62 and 63 by heat exchange with LNG from lines 92 and 119, respectively, and fed to the first fractionation column 64 at a temperature of approximately −33° C. First fractionation column 64 is equipped with reflux condenser 65 to provide reflux for the column by heat exchange of the column overhead with LNG flowing into the condenser from line 102; reboil vapor is provided in the column by reboiler 66 heated by medium pressure (75 psig) steam entering in line 129. In first fractionation column 64 the absorber column bottoms liquid is fractionated to recover overhead containing a lower fraction of acetylene, e.g. about 2 mole %, which is returned to the absorber column 56 as recycle therefor in line 132. The bottoms stream recovered from the first fractionation column, containing a higher fraction of acetylene, e.g. about 4 mole %, is discharged in line 68 and introduced therefrom into the second fractionation column 70 for fractionation therein to recover acetone bottoms and overhead gas containing acetylene. Partial condensation of the overhead for reflux for the second fractionation column is provided by cooling water in line 233 flowing through condenser 71 and reboil heat input to the column is provided by 15 psig steam in line 130 flowing through reboiler 72. The bottoms stream recovered from the second fractionation column, containing essentially pure acetone, is discharged in line 74 and sequentially cooled in heat exchangers 75 and 76 to a temperature of approximately −33° C. by heat exchange with LNG flowing in lines 121 and 115, respectively. The cooled acetone bottoms, at a pressure of 270 psig, is then separated into two parts, with the first part being returned to the absorber column 56 by line 61 as the acetone feed therefore, and the second part being flowed in line 69 to the first fractionation column as recycle to assist the separation therein. The overhead gas recovered from the second fractionation column, containing 75% acetylene and 25% acetone, flows by line 73 through heat exchanger 77, wherein the overhead gas is cooled by heat exchange with LNG flowing in line 115. The resulting two-phase mixture enters phase separator 78, wherein condensate is separated from the cooled overhead gas. Separated condensate is discharged from the phase separator by line 80 and returned to the second fractionation column as recycle therefor. This recycle has a composition of approximately 61% acetone and 39% acetylene and is at a temperature of −33° C. The cooled overhead gas is removed from separator 78 in line 79 and passed through heat exchanger 81 for further cooling therein by heat exchange with LNG flowing in line 103 to condense substantially all acetone in the overhead. The further cooled partially condensed overhead enters phase separator 82 and is separated therein to produce a further cooled overhead gas comprising substantially pure (99+mole %) acetylene, discharged in line 83, and a condensed liquid portion which is returned in line 84 to separator 78 to effect a more complete separation therein. The substantially pure acetylene product gas discharged in line 83 is initially at a temperature of −67° C. and may be suitably heat exchanged to recover its refrigeration before being sent to bottling or final use facilities.

The flows of LNG refrigerant in the illustrative ethylene plant discussed above will now be described more particularly with reference to FIG. 1. Five principal levels of refrigeration are provided by LNG flowing in the header lines 86, 100, 109, 118 and 93 at temperatures of −158° C., −121° C., −101° C., −44° C. and −26° C., respectively. Liquefied natural gas, at a temperature of approximately −158° C. and pressure of 700 psig, enters at 85 and flows into the low temperature header 86, from which the two branch streams are withdrawn in lines 87 and 88. The LNG in line 87 is flowed through the consecutive heat exchangers 31, 26, 22 and 17, thereby providing the four lower levels of refrigeration in the forecooling recovery section 133. LNG leaving the final exchanger 17 has been warmed to −101° C. and is returned from the forecooling section in branch line 87 to the −101° C. header line 109. Branch line 88 withdrawn from the low temperature header line 86 is passed through condenser 42 to partially condense the overhead of demethanizer column 41 for reflux, whereby the refrigerant stream is warmed to a temperature of approximately −121° C. for flow into the −121° C. header line 100.

Two branch streams are withdrawn from −121° C. header line 100. LNG is withdrawn from header line 100 and flowed through branch line 102 into condenser 65 to cool the overhead of first fractionation column 64 and provide reflux therefor. The refrigerant leaving the condenser in the return section of the line 102 has been warmed to approximately −101° C. and is discharged from line 102 into the header line 109 at that temperature (−101° C.). The stream of LNG withdrawn from header line 100 in branch line 103 is passed through heat exchanger 81 to cool the uncondensed gas from phase separator 78 in line 79 while simultaneously warming the LNG to about −101° C. Line 103 is subsequently joined with line 114 withdrawn from the −101° C. header line 109 to provide a combined stream of LNG in line 115 at −101° C. which is heat exchanged in exchanger 77 with the recovered overhead from the second fractionation column in line 73, thereby warming the LNG to −44° C. The warmed LNG exiting exchanger 77 is flowed to the −44° C. header line 118.

Seven branch streams, including the stream of line 114 described hereinabove are withdrawn from the −101° C. header line 109. Branch line 89 conveys LNG from the −101° C. header line to the depropanizer column reflux condenser 8, wherein the LNG cools the column overhead for partial condensation thereof and is concommitantly warmed to −44° C. The warmed LNG leaving condenser 8 in line 89 is joined by line 90 containing additional LNG at −44° C. from header line 118 and the combined refrigerant stream flows in line 91 through drip still column reflux condenser 13. LNG refrigerant is warmed to −26° C. in condenser 13 and discharged through line 91 to the −26° C. header line 93. Branch stream 101 is withdrawn from the −101° C. header line, flowed through reflux condenser 37 of the prefractionation column 36 and, at a temperature of −44° C., introduced to header line 118. Branch streams 106 and 108 are also withdrawn from the −101° C. header line 109 and flowed through deethanizer reflux condenser 52 and ethylene column reflux condenser 47, respectively, for warming therein to −44° C. prior to being flowed to the −44° C. header line 118.

In the acetylene removal complex, branch streams 110 and 112 are withdrawn from the −101° C. header line 109. The LNG in branch line 110 is passed through the reflux condenser 57 of absorber column 56 to partially condense overhead therein while simultaneously warming the LNG to −44° C. for introduction into header line 118. Branch line 112 is in turn split into branches 115 and 119. The former flows through heat exchanger 76 to cool the recovered bottoms stream from the second fractionation column in line 74 and then is joined with LNG from line 120 at a temperature of −44° C. The combined stream flows in line 121 through heat exchanger 75 for initial cooling of the bottoms streams in line 74 and is discharged at −26° C. to header line 93. LNG in the other branch line 119 derived from line 112 is passed through heat exchanger 63 for final cooling of the recovered absorber bottoms in line 60 and joined with LNG at −44° C. from line 118.

In the high temperature LNG header line 93, the LNG streams at −26° C. flowing through branch lines 91, 92 and 121 are collected and flowed to the discharge segment of the header line having control valve 96 therein, at which the LNG may be diverted to the heat exchanges represented by heat exchanger 94 for warming to approximately −3° C. for discharge at 132 to a pipeline or other distribution means (not shown). Heat exchanger 94 schematically represents various high temperature heat exchanges upstream of the forecooling section of the ethylene plant, as for example cooling of a butadiene-containing stream derived from the bottoms liquid discharged from drip still column 12 in line 15, which have been omitted for the sake of simplicity from the flow sheet of FIG. 1. These high temperature heat exchanges permit greater refrigeration effectiveness to be achieved from the liquefied natural gas than would otherwise be realized in the absence of such steps, but the practice of such high temperature heat exchange steps is not an essential feature of the present invention and the LNG collected in header line 93 could alternatively be finally warmed to discharge temperature by heat exchange with any other suitable heat transfer streams either within or without the illustrative ethylene process, as for example with cooling water streams in the FIG. 1 system.

Figure 1C:
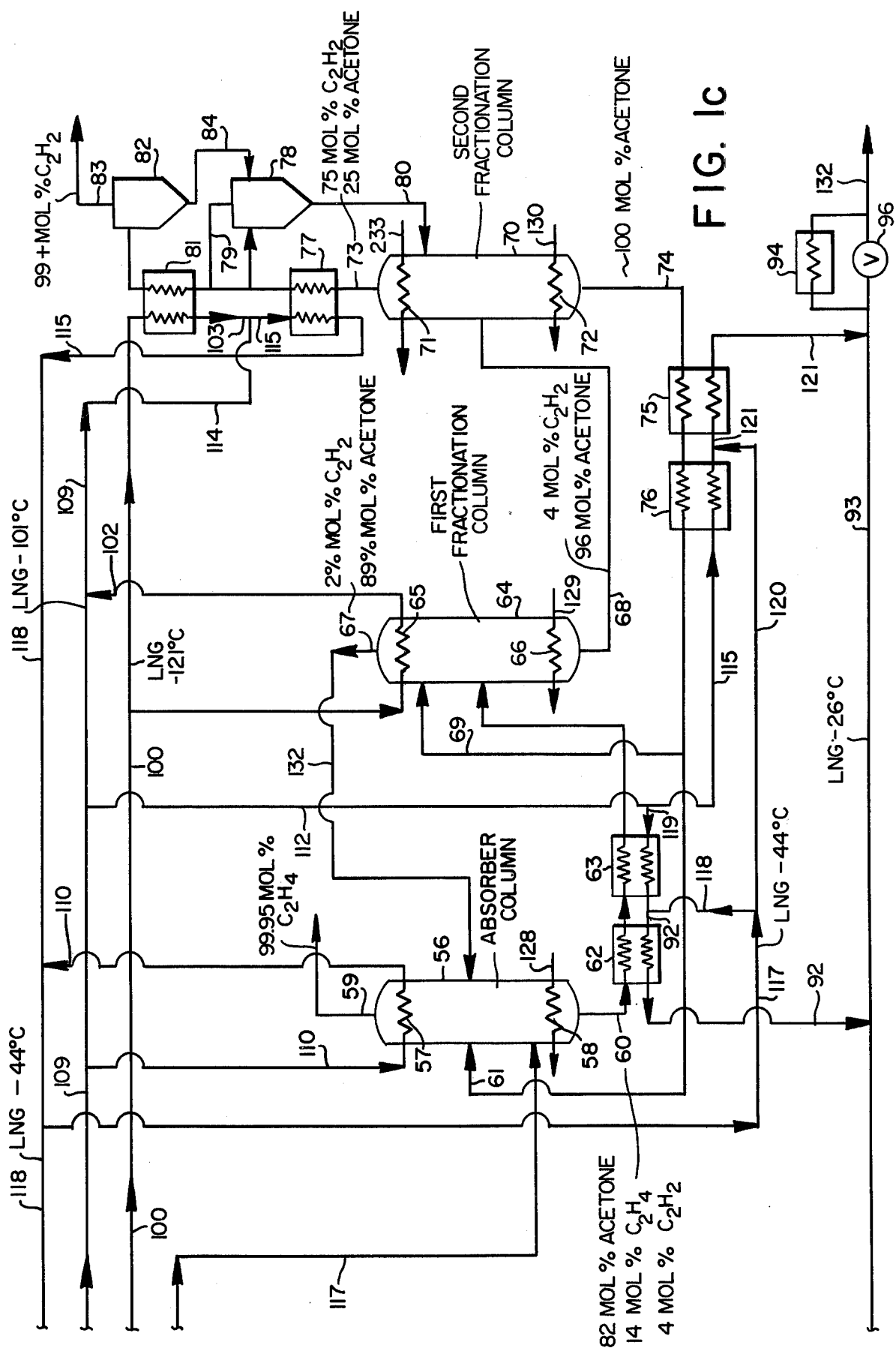
Figure 2:
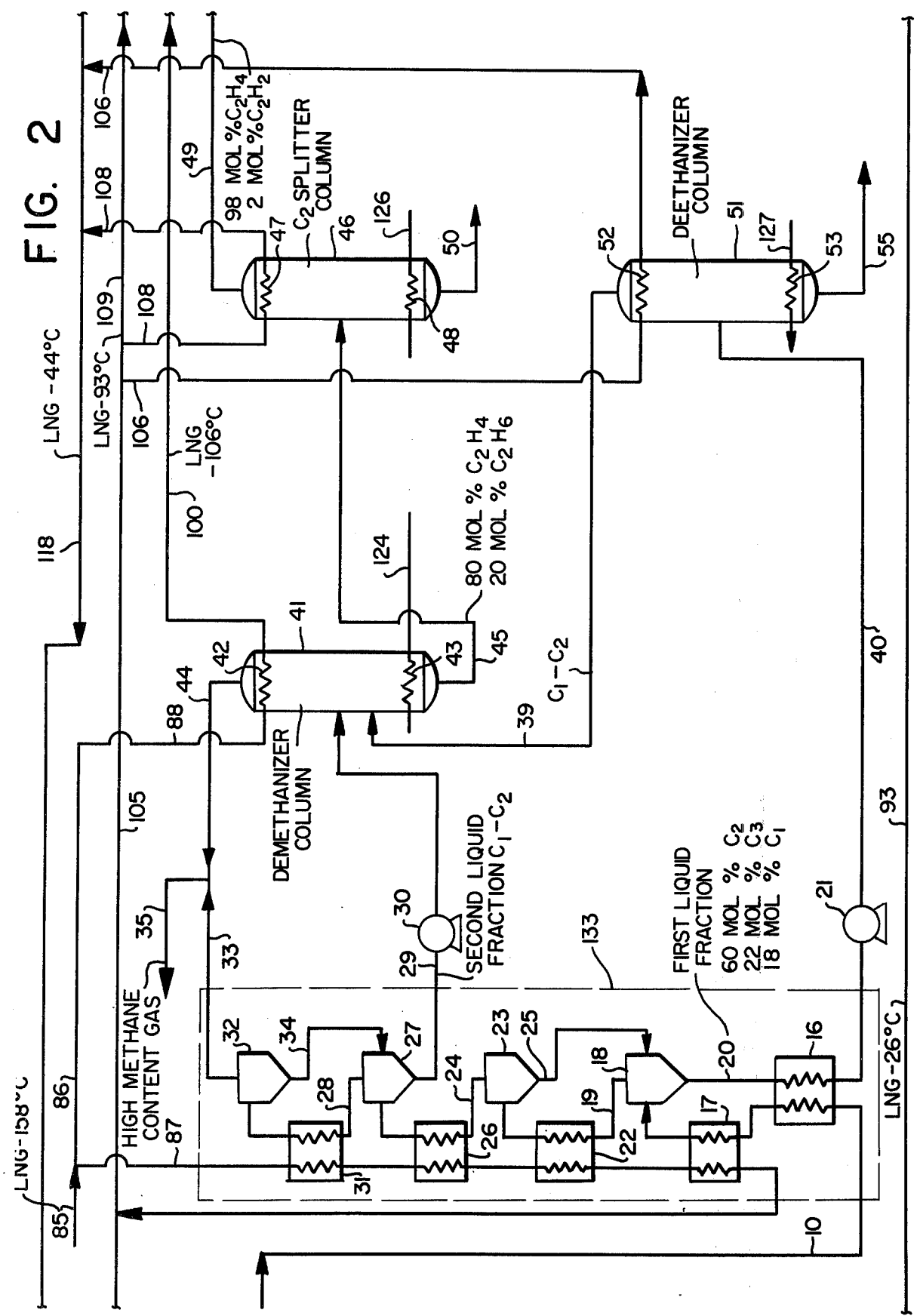
FIG. 2 is a partial schematic flowsheet of an ethylene plant employing LNG as a source of refrigeration according to another embodiment of the invention.

FIG. 2 is a partial schematic flowsheet of an ethylene plant employing LNG as a source of refrigeration according to another embodiment of the invention. FIG. 2 represents a modification of the ethylene plant section shown in FIG. 1b which is otherwise adapted to the sections of the ethylene plant as shown in FIGS. 1a and 1c. The modification of the ethylene plant shown in FIG. 2 involves the elimination of the prefractionation column from the FIG. 1b process. In this modified arrangement, the first liquid fraction which has been pumped to a second higher-than-first superatmospheric pressure in pressurizing pump 21 is passed in line 40 to the deethanizer column 51 and fractionated to recover a $C_1$–$C_2$ overhead and a $C_3$ bottoms. The recovered $C_1$–$C_2$ overhead is passed in line 39 to demethanizer column 41 and fractionated therein with the second liquid fraction entering from line 29 to recover demethanizer overhead comprising methane in line 44 and a demethanizer bottoms comprising $C_2$ constituents in line 45.

From line 45 the demethanizer bottoms comprising 80 mol % ethylene and 20 mol % ethane is introduced to the $C_2$ splitter column 46 and fractionated to recover ethylene as overhead product in line 49 and ethane bottoms in line 50. As before, the $C_3$ bottoms recovered from the deethanizer column 51 in line 55, comprising predominantly propylene and propane, may be fractionated in a $C_3$ splitter column (not shown) to recover propylene as overhead product.

Relative to the ethylene plant arrangement shown in FIG. 1b, the modification of FIG. 2 transfers the fractionation load associated with the prefractionation column in the FIG. 1b process to the demethanizer column in the FIG. 2 scheme. With such change, the reflux condenser 42 of the demethanizer column has a correspondingly increased refrigeration load in the FIG. 2 arrangement—from about $2.3 \times 10^6$ BTU/hr. in the FIG. 1b process to approximately $8.6 \times 10^6$ BTU/hr. in the FIG. 2 arrangement—and thus requires a correspondingly increased LNG flow rate in line 88 through the reflux condenser. The increased refrigeration requirement for the demethanizer column is readily available due to the elimination of the reflux condenser duty, as associated with the deleted prefractionation column, with only minor change to LNG refrigerant temperatures in the header lines. In the FIG. 2 system, the LNG refrigerant temperature in header line 109 is increased from −101° C. to −93° C. and the LNG refrigerant temperature in header line 100 is increased from −121° C. to −106° C., while the refrigerant temperatures in all other LNG header lines remain in the same as in the FIG. 1b flowsheet.

Figure 3:
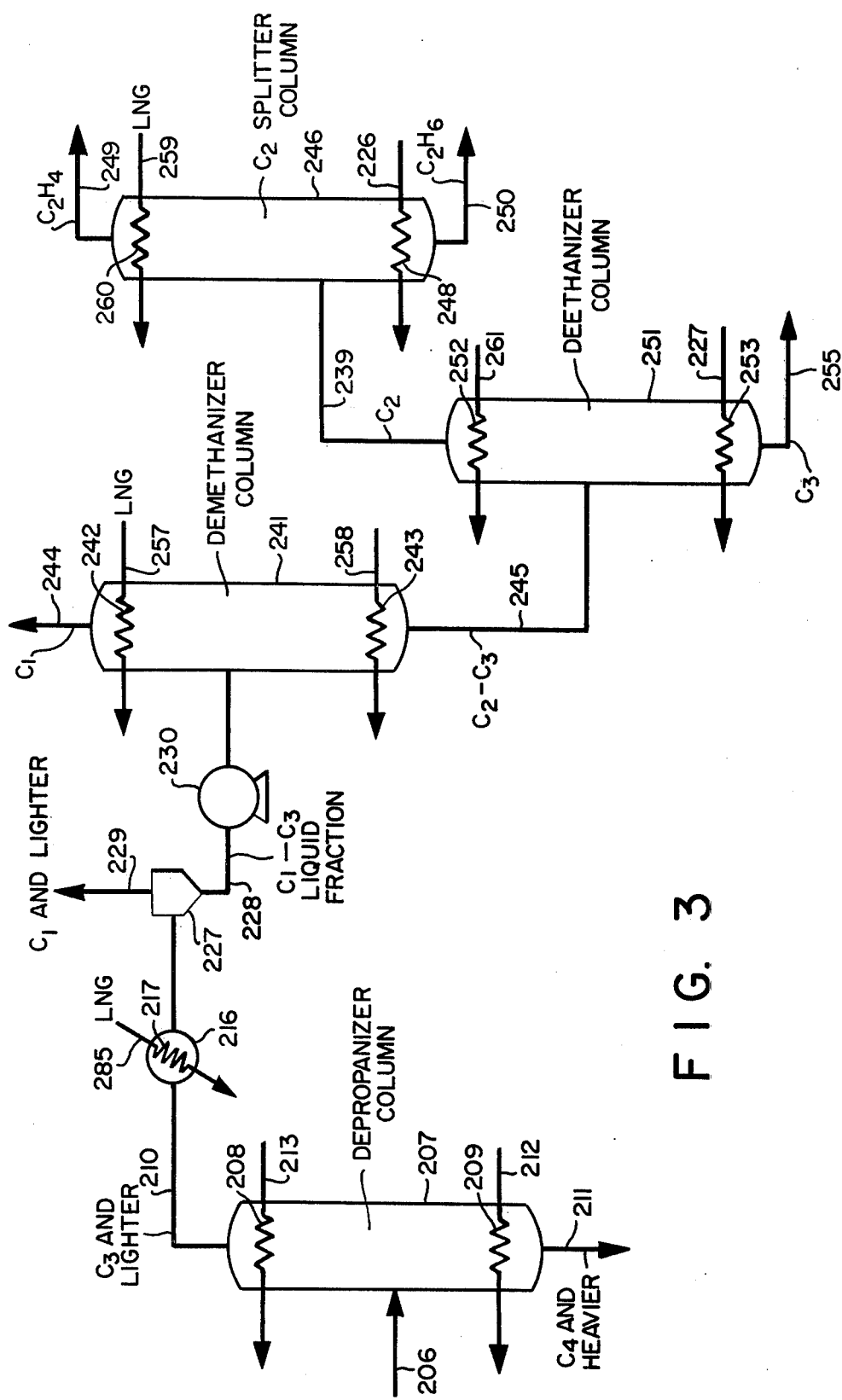
FIG. 3 is a schematic flowsheet of an ethylene plant employing LNG as a source of refrigeration according to still another embodiment of the invention.

FIG. 3 is a schematic flowsheet of an ethylene plant employing LNG as a source of refrigeration according to still another embodiment of the invention. In this embodiment the hydrocarbon feed gas mixture comprising at least $C_1$–$C_4$ constituents including ethylene enters the process at superatmospheric pressure in line 206 and is fractionated in depropanizer column 207 to recover overhead gas comprising $C_3$ and lighter constituents in line 210 and bottoms comprising $C_4$ and heavier constituents in line 211. Reflux is condensed for the depropanizer column by heat exchange of the depropanizer overhead with LNG refrigerant flowing in line 213 through the reflux condenser 208. Reboil vapor is generated in the depropanizer column by steam flowing in line 212 through the reboiler 209 of the column.

The overhead gas recovered from the depropanizer column in line 210 is cooled in heat exchanger 216 by externally supplied LNG flowed through refrigerant passage 217 in the heat exchange from line 285. This cooling of the overhead gas recovered from the depropanizer column is carried out to condense a liquid fraction comprising $C_1$–$C_3$ constituents which is separated from the uncondensed gas in phase separator 207. The uncondensed gas, comprising $C_1$ and lighter (e.g., hydrogen) constituents is withdrawn from the phase separator in line 229 and may be recycled to the cracking furnaces of the ethylene plant as fuel therefor or else passed to other treatment and/or final disposition steps as desired.

The condensed liquid fraction is withdrawn from phase separator 227 in line 228 and pressurized by pressurizing pump 230 to a superatomspheric pressure higher than the pressure of the feed gas mixture to the process. From line 228 the pressurized liquid fraction is fractionated in demethanizer column 241 to recover a demethanizer overhead comprising methane in line 244 and a demethanizer bottoms comprising $C_2$–$C_3$ constituents. Externally supplied liquefied natural gas is flowed through line 257 and heat exchanged with the demethanizer overhead in reflux condenser 242 to condense the demethanizer overhead and provide reflux for the demethanizer column while warming the liquefied natural gas. Reboil vapor is generated for the demethanizer column by steam flowing in line 258 through reboil heat exchanger 243.

The demethanizer bottoms recovered from the demethanizer column in line 245 is flowed to the deethanizer column 251 and fractionated to recover a $C_2$ overhead in line 239 and a $C_3$ bottoms in line 255. Reflux is condensed for the deethanizer column by LNG refrigerant flowing through reflux condenser 252 from line 261, while vapor is generated in the lower section of the column by steam from line 227 flowing through reboil heat exchanger 253. The $C_2$ overhead recovered from the deethanizer column is flowed through line 239 to the $C_2$ splitter column 246 and fractionated to recover ethylene is overhead product in line 249 and ethane bottoms in line 250. Externally supplied LNG from line 259 is heat exchanged in reflux condenser 260 with the $C_2$ splitter column overhead to condense same and provide reflux for the column while warming the liquefied natural gas. Steam in line 226 flowing through reboil heat exchanger 248 provides vaporization boil-up for the $C_2$ splitter column.

The various illustrative embodiments of the invention described above employ LNG as a source of refrigeration to satisfy all of the refrigeration requirements of the ethylene plant which are conventionally accommodated by ethylene/propylene refrigeration systems. Such application of LNG to the total refrigeration requirements in the ethylene plant is highly effective and economical, as will be shown more fully hereinafter. Nonetheless, in some cases it may not be possible to obtain LNG at a rate sufficient to provide for all of the refrigeration requirements of a particular ethylene plant. In such event alternative embodiments of the invention may be employed wherein LNG is used to satisfy the lowest temperature refrigeration requirements of the ethylene production process, thereby eliminating the conventional ethylene refrigeration system and the most expensive portion of the coventional propylene refrigeration system. A small part of the conventional propylene system is retained to satisfy some of the refrigeration requirements of the ethylene plant at intermediate temperature levels, while operating the forecooling recovery section at lower temperature and pressure levels than conventionally practiced and maintaining the final separation section at conventional operating conditions.

As an illustrative example under the foregoing discussion, the flowsheet of the invention shown in FIG. 1 may be suitably modified for the practice of an alternative embodiment of the invention employing partial refrigeration with LNG simply by deletion of the LNG branch streams 101, 106, and 110 providing refrigeration for overhead reflux condensation for the prefractionation column 36, deethanizer column 51, and absorber column 56, respectively. In place of the deleted LNG refrigerant streams, propylene refrigeration is supplied to the prefractionation column, deethanizer and absorber column in a conventional manner; all other LNG flow streams remain the same as shown in FIG. 1. In this modified alternative embodiment, the LNG temperatures in the respective header lines 100, 109, 118 and 93 will be $-105°$ C., $-82°$ C., $-43°$ C. and $-18°$ C., slightly higher than in the unmodified case in order to use the partial LNG refrigeration most effectively. In actual practice of the modified embodiment, propylene refrigerant may suitably be used to provide some small additional cooling of the bottoms recovered from second fractionation column 70 in line 74 prior to the flow of the bottoms through exchanger 75, thus achieving the most efficient usage of LNG in exchangers 75 and 76 for cooling the bottoms stream.

Despite minor alterations in refrigerant temperature levels, the usage of LNG to satisfy a portion of the ethylene plant total refrigeration requirements in the manner described above allows the ethylene plant to be operated at the same advantageous process conditions as when LNG supplies all of the refrigeration requirements of the plant, i.e., with the forecooling recovery section operating at a low pressure as for example 125 psig, while the final separation is at conventional high pressures, e.g. 500 psig. In the practice of this invention, these process advantages can be economically achieved even when LNG is used as refrigerant only in the forecooling recovery section and in the reflux condensers of the demethanizer and $C_2$ splitter (ethylene) columns; however, such implementation represents a practical minimum usage lever for the LNG. Further curtailment of LNG usage level while attempting to maintain the beneficial process conditions characteristic of this invention tends to be uneconomical and to yield poor overall utilization of the LNG refrigeration. In this regard, it is apparent that the method of the present invention may be employed in an ethylene plant not having a low-temperature scrubbing acetylene removal complex as herein described, but that the provision of such a complex facilitates particularly high utilization of the LNG refrigeration and obviates additional warming of the LNG outside of the ethylene plant which might be necessary in some cases for ultimate regasification of the LNG.

As discussed hereinabove, the improvement achieved by the present invention derives from operating the forecooling section of the ethylene plant at much lower pressure than is conventionally employed, as for example 125 psig, while operating the final separation section at conventionally high pressure levels. Such change allows a lowering of operating temperature in the forecooling section, with the result that the cooling and warming curves for the overall system are better matched than they would be if the ethylene plant were operated at uniform high pressure while using LNG refrigeration. The better matching of curves indicates that the heat transfer inefficiencies and irreversibilities in the process scheme of this invention are much lower than in the above high pressure case; a much more efficient utilization of the LNG refrigeration potential is therefore realized in the former instance. The conventional high pressure levels in the final separation section are attained in this invention by employing pressurizing pumps on the liquid feed streams from the forecooling recovery section to the final separation section. Such pressurization involves only a very small fraction of the power which is required for gas compression; it thus permits substantial economies to be realized in providing the high separation pressures which are necessary for good overall LNG utilization.

To demonstrate the comparative advantages of the invention over ethylene plants with conventional refrigeration and ethylene plants with LNG refrigeration operating at uniform high pressures, a number of illustrative examples will be presented below. Examples I, II, IV, V AND VI are based on an ethylene plant having an equipment sequence as shown in FIG. 1, and Example III is based on an ethylene plant having an equipment sequence as described in connection with FIG. 2, each with a front-end depropanizer column, forecooling recovery section, final separation section and acetylene removal complex. Each of the examples is based on the processing of 297,600 lbs. of cracked naphtha feedstock per hour to yield 500 million lbs. per year of ethylene and 400 million lbs. per year of propylene at purities of 99.96 mole % and 95 mole %, respectively. The cracked naphtha feedstock is illustratively assumed to have a dry molar composition of hydrogen — 10%, methane — 25%, ethylene — 26.4%, ethane — 6.4%, acetylene — 0.5%, propylene — 16.6%, propane — 1%, $C_4$'s — 6.3%, $C_5$'s — 2.7%, $C_6$-$C_8$ — 4.4%, and $C_9+$ — trace. The LNG refrigerant in Examples II-VI is assumed to have the following molar composition: methane — 89.2%, ethane — 7.8%, propane — 2.5%, iso-butane — 0.2% and normal butane — 0.3%, and to be available at a pressure of 700 psig.

EXAMPLE I

An ethylene plant having an equipment sequence as illustrated in FIG. 1 employing conventional ethylene/propylene refrigeration and operating at conventional high pressure throughout the process will now be described as a comparative basis for the further examples presented hereinafter.

In this conventional plant, refrigeration is supplied by propylene at temperature levels down to about −40° C. and by ethylene at levels down to about −100° C. In the propylene system, three levels of refrigeration are generally provided. Propylene refrigerant vapors enter the suction of the propylene refrigeration compressor and are compressed therein to high pressure, e.g. 250 psig, and are discharged to water-cooled condensers. The resulting condensed liquid is further cooled by heat exchange with ethylene process streams and flows to the highest temperature heat exchangers and a first flash tank. Liquid from the first flash tank flows to process heat exchangers requiring refrigeration at the intermediate temperature levels of the propylene system, and passes to a second flash tank. Liquid from the second flash tank flows to process heat exchangers requiring refrigeration at the lowest temperature levels of the propylene system. The vapors from the process heat exchangers and the flash tanks are returned to the propylene refrigeration compressor.

In the ethylene refrigeration system, two refrigeration levels are supplied. The workings of the ethylene system are similar to those of the propylene system, with the high pressure ethylene compressor discharge being condensed by heat exchange with propylene refrigerant.

This plant operates at high pressure throughout, with the cracked furnace gas being compressed to 550 psig. The total refrigeration requirement of this plant is 135.6 million BTU/hr., with the requirements at each level as follows:

| Temperature, °C | Refrigeration Requirement, $10^6$ BTU/hr. |
|---|---|
| −101 | 8.780 |
| −72 | 8.342 |
| −40 | 86.950 |
| −15 | 28.650 |
| 0 | 2.900 |

Figure 4:
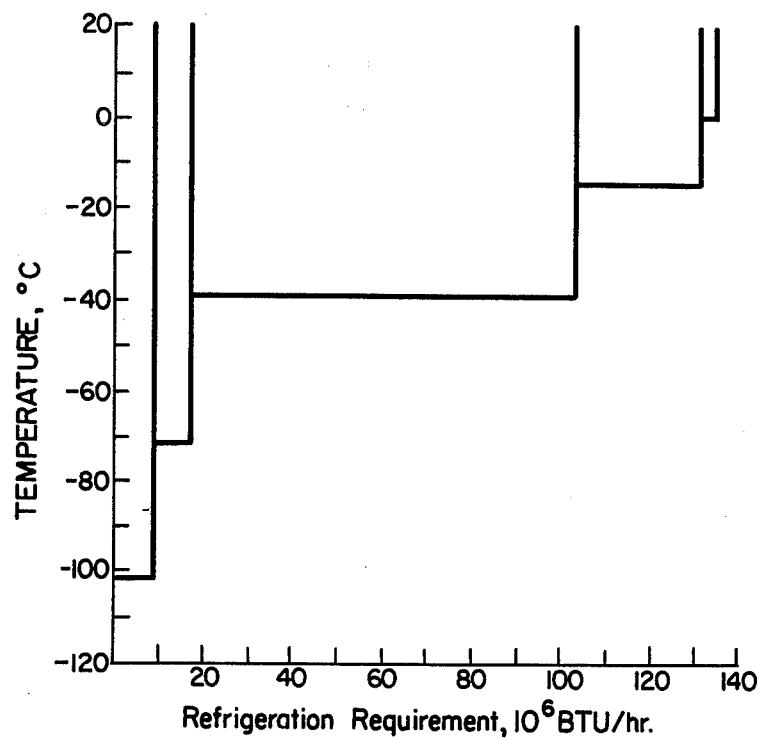
FIG. 4 is a graph of the refrigeration requirements for an ethylene plant using a conventional ethylene-propylene refrigeration system and operating at high pressure throughout.

FIG. 4 herein shows a plot of the above data; this graph represents the cooling curve of the refrigeration requirements for the ethylene plant. Associated with these refrigeration levels are power requirements of 19,800 brake horsepower (bhp) for the propylene refrigeration compressor and 3,700 bhp for the ethylene refrigeration compressor. The total power expenditure for the refrigeration system is thus quite large, being roughly equal to the power which is needed for the compression of the cracked furnace gas to 550 psig, which is 22,700 bhp, for an overall total of 47,200 bhp for the ethylene plant.

In this conventional ethylene plant, as well as in all ethylene plants to be illustratively described in connection with the remaining Examples, steam is generated by the quenching and cooling of the hot gas effluent from the feedstock cracking furnaces. This steam is employed to drive the various (furnace gas and refrigeration) compressors in the system. Such steam may also be used in the reboiler heat exchangers for the various ethylene plant separation columns as the heating medium therefor. Nonetheless, it is generally more desirable to employ propylene refrigerant in place of steam as the reboiler heating medium for the demethanizer and $C_2$ splitter columns, and for the prefractionation column, if employed, thereby cooling the refrigerant in the respective boilers and realizing refrigeration credits from the heat exchanges. Such usage of propylene refrigerant for cooling credits is assumed for the ethylene plant in this Example, as well as for the ethylene plant of Example IV and VI described hereinbelow wherein partial refrigeration with propylene refrigerant is employed.

EXAMPLE II

In this example, LNG is implemented as a source of refrigeration in accordance with this invention in the manner described in connection with FIG. 1 herein to satisfy all of the refrigeration requirements of the ethylene plant. LNG is supplied to the ethylene plant as refrigerant at a rate of 240 million standard cubic feet per day. The pressure level in the forecooling recovery section of the ethylene plant is reduced from the 550 psig level characteristic of the conventional plant of Example I to 125 psig, making possible the reduction in furnace gas compression requirements from 22,700 bhp to 13,850 bhp. Thus the dryers 4 and 5, the depropanizer column 7, drip still column 12 and the subsequent forecooling recovery section 133 all operate at 125 psig. The remainder of the plant comprising the final separation section and the acetylene removal complex is operated at conventional high operating pressure to minimize the required refrigeration. For this purpose, pumps 21 and 30 are employed to feed the first and second liquid fractions to the prefractionation column 36 and the demethanizer column 41, respectively.

Figure 5:
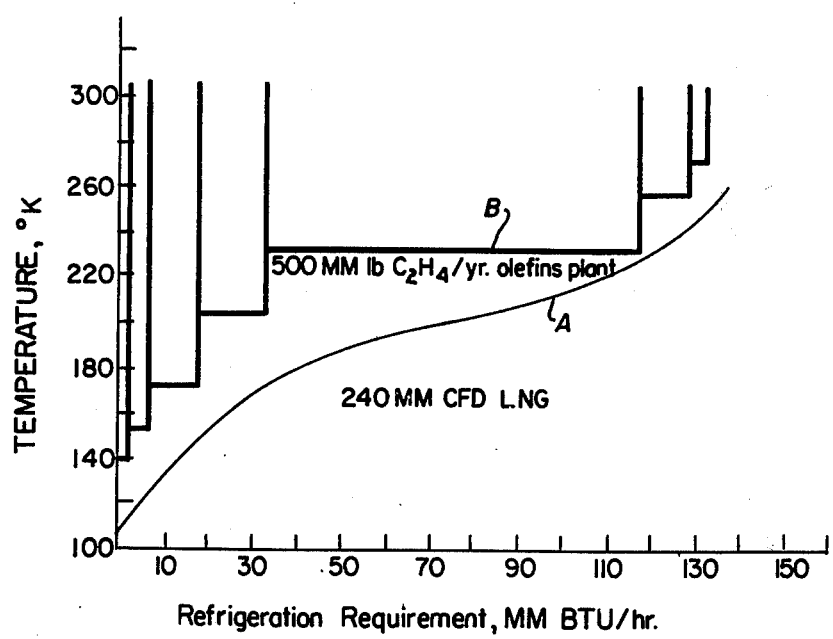
FIG. 5 is a graph of the respective cooling and warming curves for the ethylene plant and LNG refrigerant of the FIG. 1 embodiment of the invention.

The cooling and warming curves for this Example are shown in FIG. 5 wherein the refrigeration requirement in $10^6$ BTU/hr. is plotted against the temperature level in °K. Curve A is the warming curve for LNG at a pressure of 700 psig supplied at the rate of 240 million standard cubic feet per day. Curve B is the cooling curve showing the refrigeration requirements for the ethylene plant. As shown by the graph, an efficient matching of the respective curves is achieved by the method of this invention without excessively small temperature differentials between the curves such as would require prohibitively large amounts of heat exchanger area and without extremely large temperature differences which would waste the LNG refrigeration potential. The cooling curve for this Example exhibits a 20°-30° C. lowering of temperature in the forecooling recovery section of the ethylene plant below that of Example I, and this is easily accommodated by the LNG refrigerant. By wholly eliminating the refrigeration system compression requirements, this embodiment of the invention achieves a total power saving of 32,350 bhp over the conventional ethylene plant of Example I.

EXAMPLE III

LNG is utilized in this Example as a source of refrigeration in the manner described in connection with FIG. 2 herein to satisfy all of the refrigeration requirements of the ethylene plant. As in Example II, LNG is supplied to the ethylene plant as refrigerant at a rate of 240 million standard cubic feet per day, the forecooling recovery section of the plant is operated at 125 psig and the final separation section and acetylene removal complex are operated at conventional high pressure levels. The power savings in furnace gas compression requirements relative to the Example I plant are the same in this case as in Example II.

Figure 6:
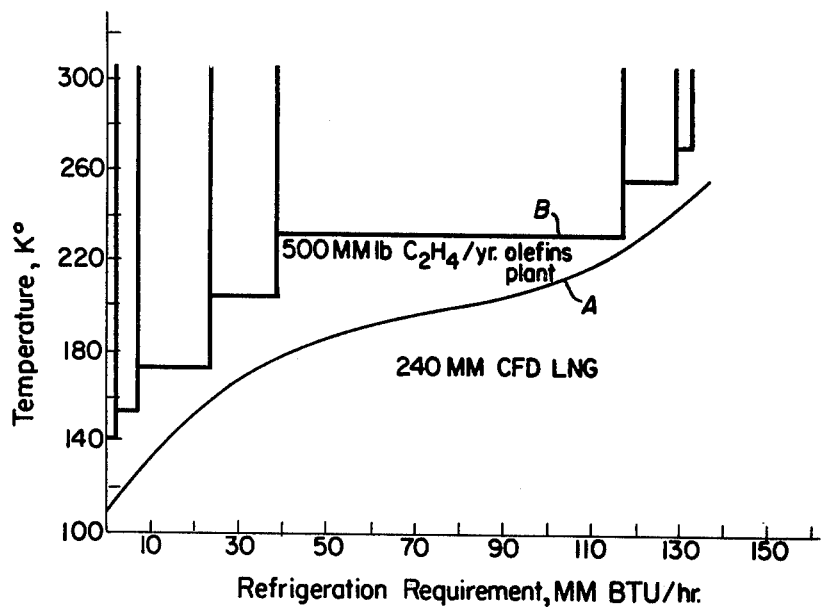
FIG. 6 is a graph of the respective cooling and warming curves for the ethylene plant and LNG refrigerant of the FIG. 2 embodiment of the invention.

The cooling and warming curves for this Example are shown in FIG. 6. On this graph the refrigeration requirement in $10^6$ BTU/hr. is plotted against the temperature level in ° K. Curve A is the LNG warming curve for a refrigerant pressure level of 700 psig and a flow rate of 240 million cubic feet per day. Curve B is the cooling curve showing the refrigeration requirements for the ethylene plant. As compared with the cooling curve in FIG. 5 for Example II, the cooling curve in this case exhibits an increased refrigeration requirement at the temperature level of approximately 172° K. (−101° C.). Such relative increase in low temperature refrigeration requirement is a consequence of the previously described elimination of the prefractionation column in the FIG. 2 system as associated with a corresponding increase in the refrigeration load on the demethanizer column at the low temperature level. As shown in FIG. 6, an efficient matching of the cooling and warming curves is achieved by the process integration in this Example. The embodiment of this Example also achieves a total power saving of 32,250 bhp over the conventional ethylene plant of Example I.

EXAMPLE IV

This Example employs LNG refrigeration according to the present invention to satisfy a major portion of the refrigeration requirements of the ethylene plant. LNG refrigerant is supplied to the process at the rate of 150 million standard cubic feet per day. This quantity of refrigeration permits elimination of the conventional ethylene refrigeration system and the most expensive portion of the propylene refrigeration system. LNG is flowed through the various heat exchangers of the ethylene plant in the manner illustratively described hereinearlier in connection with the alternative "partial refrigeration" modified embodiment of the process shown in FIG. 1, wherein the LNG branch streams to the depropanizer column, prefractionation column, deethanizer column, and absorber column overhead reflux condensers are deleted and replaced by conventional propylene refrigeration. As in Example II, the dryers, depropanizer, drip still and forecooling section operate at 125 psig; the final separation section is maintained at conventional high pressure. This arrangement requires 6,100 bhp for the propylene refrigeration compressor; total power requirements for the refrigeration system have thus been reduced from 23,500 bhp, as in Example I, to 6,100 bhp. The total power savings for this system is 26,250 bhp over the conventional ethylene plant of Example I.

Figure 7:
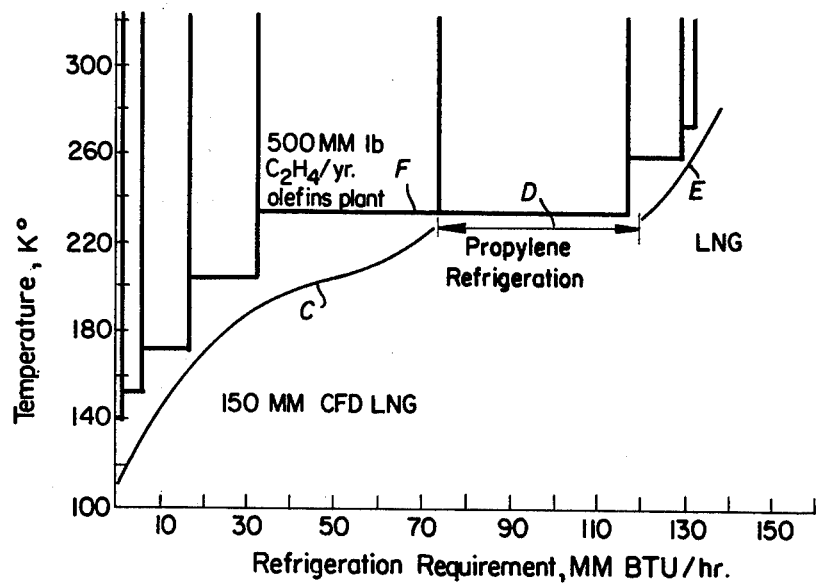
FIG. 7 is a graph of cooling and warming curves for the ethylene plant and LNG refrigerant of another embodiment of the invention wherein the LNG supplies only a portion of the total refrigeration requirements of the ethylene plant.

The cooling and warming curves for this Example are shown in FIG. 7. Curve F is the cooling curve showing the refrigeration requirements for the ethylene plant. The LNG warming curve in this case is comprised of the two segments C and E. Segment C represents the refrigeration which is supplied by the LNG over the temperature range from 110° K. (−163° C.) to approximately 230° K. (−43° C.), while segment E is the warming curve for the LNG refrigerant at temperatures above 230° K. (−43° C.). Segment D of the warming curve represents the remaining 44.5 million BTU/hr. which is supplied by the propylene refrigeration system retained in this case to augment the LNG. Propylene refrigerant is used to supply the refrigeration requirements of the absorber, prefractionator, deethanizer and depropanizer columns and to supply some additional cooling for the bottoms recovered from the second fractionation column 70 upstream of the heat exchanger 75. FIG. 7 shows a close matching between the cooling curve of the ethylene plant and the LNG warming curves over the full respective temperature ranges.

EXAMPLE V

Figure 8:
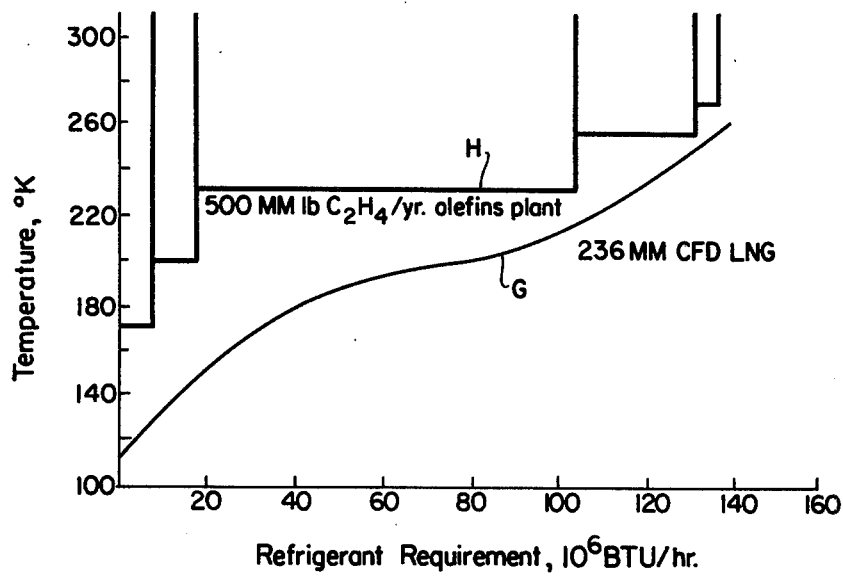
FIG. 8 is a graph of cooling and warming curves for an ethylene plant using LNG to supply the total refrigeration requirements, but operating at high pressure throughout.

In this Example the ethylene plant operates under conventional (high pressure) conditions except that the total refrigeration requirements of the plant are supplied by LNG. The cooling and warming curves for this Example are shown in FIG. 8, wherein curve G is the warming curve for LNG at a pressure of 700 psig supplied at the rate of 236 million standard cubic feet per day. Curve H is the cooling curve showing the refrigeration requirements of the ethylene plant in which the cracked naphtha feedstock is compressed to an initial level of 550 psig. LNG is discharged from the refrigeration system of the ethylene plant at 260° K. (−13° C.). Although all refrigeration for the ethylene plant is supplied by LNG in this case, FIG. 8 shows that rather large temperature differences exist between the cooling and warming curves over the entire temperature range up to about 240° K. (−33° C.). As discussed earlier herein, such large temperature differences are associated with correspondingly large heat transfer energy losses which are severely detrimental to the utilization efficiency for the LNG refrigeration. The power savings achieved by this process through elimination of the propylene and ethylene refrigeration compressors amounts to 19,800 bhp and 3,700 bhp, respectively, for a total power savings of 23,500 bhp over the conventional ethylene plant of Example I.

EXAMPLE VI

Figure 9:
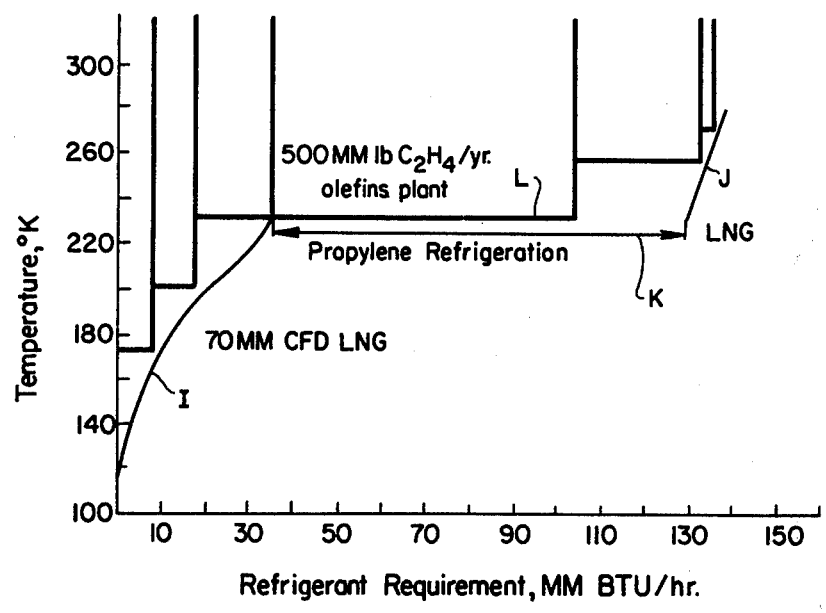
FIG. 9 is a graph of cooling and warming curves for an ethylene plant using LNG to supply a portion of the total refrigeration requirements, but operating at high pressure throughout.

This Example is based upon substitution of LNG refrigeration for the ethylene refrigeration system and part of the propylene refrigeration system. As in Example V, the ethylene plant is operated at conventional high pressure levels, with cracked furnace gas compression to 550 psig. LNG refrigerant is supplied to the heat exchange system of the ethylene plant at a rate of 70 million standard cubic feet per day. This LNG flow rate represents the minimum LNG requirement for the high pressure ethylene plant; as shown by the cooling and warming curves for this case in FIG. 9, any lower flow rate of LNG would shift the LNG warming curve segments I and J to the left, with the result that the LNG would not be able to supply the ethylene plant refrigeration requirements. Although the cooling curve L in FIG. 9 shows a close match between the low temperature refrigeration requirements of the ethylene plant and the LNG provided, a rather large load (94 million BTU/hr.) of propylene refrigeration, shown as warming curve segment K, is required at the 233° K. (−40° C.) level which in turn requires 16,200 bhp for propylene refrigeration compression. As a result, the total power savings over the conventional ethylene plant of Example I is only 7,300 bhp.

Table I herein summarizes the LNG operating conditions and flow rates for each of the heat exchange steps in the above Examples II-VI. The process parameters are tabulated along with the ethylene plant refrigeration requirements associated with each step by reference to the ethylene plant heat exchangers as numbered in FIGS. 1 and 2 herein.

As shown by the foregoing, the implementation of LNG according to the present invention affords close and efficient matching between the cooling curve for the ethylene plant and the LNG warming curve, with substantial savings in system power requirements over the conventional ethylene plant employing ethylene/propylene refrigeration. Moreover, these power savings are significantly greater than can be achieved in conventional high pressure ethylene plants wherein LNG refrigeration is employed. For example, the power expenditure in Example II and III where in LNG refrigeration is employed in accordance with the present invention to satisfy all of the ethylene plant refrigeration requirements, is approximately 40% lower than the power expenditure of Example V, wherein LNG refrigeration satisfies all of the refrigeration requirements in a conventional high pressure ethylene plant, and is approximately 70% lower than the power expenditure in the conventional ethylene plant of Example I, employing ethylene/propylene refrigeration.

The comparative economic advantages for the above Examples II-VI are summarized in Table II below. Investment and operation cost savings for each of the Examples II-VI are expressed as percentages of the total investment and total operating costs for the conventional ethylene plant of Example I using ethylene/propylene refrigeration. The overall cost savings for the latter five Examples are likewise presented as percentages of the total cost for the Example I plant. Investment costs are put on a yearly basis, by annualization at 17%. The operating savings are also figured on an annual basis. Utilities for the Example I conventional ethylene plant and the LNG refrigerated plants of Examples II-VI are identical except for steam (boiler feed water) balances. Steam is generated in all cases by the quenching and cooling of the hot gas effluent from the naphtha cracking furnaces. The operating savings for the Examples II-VI have thus been taken as the net steam produced for credit, since all system compressors are assumed to be steam driven. A value for steam credits of $1.50/1000 lb. (steam at 1800 psig pressure and 482° C.; the low pressure (<100 psig) steam produced by the system is taken as 87.5% of 1800 psig steam cost) has been assumed.

TABLE I

LNG OPERATING CONDITIONS AND FLOWS FOR THE HEAT EXCHANGE STEPS IN EXAMPLES II - VI

| Heat Exchanger FIG. 1 Reference No. | Example II | | | | Example III | | | |
|---|---|---|---|---|---|---|---|---|
| | Refrigeration Requirements $10^3$ BTU/hr. | LNG Flow Rate $10^6$ SCFD | LNG Temp ° K In | LNG Temp ° K Out | Refrigeration Requirements $10^3$ BTU/hr. | LNG Flow Rate $10^6$ SCFD | LNG Temp ° K In | LNG Temp ° K Out |
| 31 | 1,050 | 210 | 115 | 117.3 | 1,050 | 171 | 115 | 117.9 |
| 26 | 5,240 | 210 | 117.3 | 128.3 | 5,240 | 171 | 117.9 | 132.7 |
| 42 | 2,480 | 30.0 | 115 | 151.8 | 8,780 | 69.0 | 115 | 166.9 |
| 22 | 8,465 | 210 | 128.3 | 146.3 | 8,465 | 171 | 132.7 | 153.3 |
| 17 | 13,990 | 210 | 146.3 | 172.1 | 13,990 | 171 | 153.3 | 181.1 |
| 65 | 1,610 | 29.4 | 151.8 | 173.0 | 1,610 | 67.7 | 166.9 | 174.4 |
| 81 | 32 | 0.6 | 151.8 | 173.0 | 32 | 1.3 | 166.9 | 174.4 |
| 76 | 1,700 | 4.8 | 172.2 | 229 | 1,700 | 5.2 | 180 | 229 |
| 47 | 38,150 | 107.5 | 172.2 | 229 | 38,150 | 116.1 | 180 | 229 |
| 77 | 550 | 1.6 | 172.2 | 229 | 550 | 1.7 | 180 | 229 |
| 63 | 850 | 2.4 | 172.2 | 229 | 850 | 2.6 | 180 | 229 |
| 57 | 15,300 | 43.1 | 172.2 | 229 | 15,300 | 46.5 | 180 | 229 |
| 37 | 6,300 | 17.8 | 172.2 | 229 | 0 | 0 | 0 | 0 |
| 52 | 5,800 | 16.3 | 172.2 | 229 | 5,800 | 17.7 | 180 | 229 |
| 8 | 16,500 | 46.5 | 172.2 | 229 | 16,500 | 50.2 | 180 | 229.0 |
| 75 | 2,900 | 57.5 | 229 | 246.5 | 2,900 | 57.5 | 229 | 246.5 |
| 62 | 3,700 | 73.4 | 229 | 246.5 | 3,700 | 73.4 | 229 | 246.5 |
| 13 | 5,500 | 109.1 | 229 | 246.5 | 5,500 | 109.1 | 229 | 246.5 |
| 94 | 2,900 | 51.0 | 246.5 | 270 | 2,900 | 51.0 | 246.5 | 270 |

| Example IV | | | | Example V | | | | Example VI | | | |
|---|---|---|---|---|---|---|---|---|---|---|---|
| Refrigeration Requirements $10^6$ SCFD | LNG Flow Rate $10^6$ SCFD | LNG Temp° K In | LNG Temp° K Out | Refrigeration Requirements $10^3$ BTU/hr. | LNG Flow Rate $10^6$ SCFD | LNG Temp ° K In | LNG Temp ° K Out | LNG Flow Rate $10^6$ SCFD | LNG Temp ° K In | LNG Temp ° K Out | |
| 1,050 | 130 | 115 | 118.4 | 1,050 | 47.9 | 115 | 125.5 | 49.0 | 115 | 124.5 | |
| 5,240 | 130 | 118.4 | 135.6 | 5,250 | 47.9 | 125.5 | 171 | 49.0 | 124.5 | 169.0 | |
| 2,480 | 20.0 | 115 | 167.9 | 2,480 | 188.1 | 115 | 121.3 | 21.0 | 115 | 165.0 | |
| 8,465 | 130 | 135.6 | 163.4 | 6,700 | 47.9 | 171 | 197.8 | 49.0 | 169.0 | 196.6 | |
| 13,990 | 130 | 163.4 | 191.3 | 1,610 | 184.5 | 121.3 | 125.5 | 20.6 | 165.0 | 187.4 | |
| 1,610 | 19.6 | 167.9 | 189.2 | 32 | 3.7 | 121.3 | 125.5 | 0.41 | 165.0 | 187.4 | |
| 32 | 0.4 | 167.9 | 189.2 | 8,100 | 47.9 | 197.8 | 216.8 | 34.9 | 196.6 | 228.8 | |
| 1,700 | 6.2 | 191 | 229.8 | 1,700 | 4.7 | 125.5 | 216.8 | 6.3 | 191.7 | 228.9 | |
| 38,150 | 138.7 | 191 | 229.8 | 38,150 | 104.6 | 125.5 | 216.8 | * | | | |
| 550 | 2.0 | 191 | 229.8 | 550 | 1.5 | 125.5 | 216.8 | 2.1 | 191.7 | 228.9 | |
| 850 | 3.1 | 191 | 229.8 | 850 | 2.3 | 125.5 | 216.8 | 3.2 | 191.7 | 228.9 | |
| 15,300 | * | | | 15,300 | 41.9 | 125.5 | 216.8 | * | | | |
| 6,300 | * | | | 6,300 | 17.3 | 125.5 | 216.8 | 23.5 | 191.7 | 228.9 | |
| 5,800 | * | | | 5,800 | 15.9 | 125.5 | 216.8 | * | | | |
| 16,500 | * | | | 16,500 | 135.9 | 216.8 | 254.3 | * | | | |
| 2,900 | 18.6 ** | 229.8 | 255.2 | 2,900 | 23.9 | 216.8 | 254.3 | * | | | |
| 3,700 | 52.8 | 229.8 | 255.2 | 3,750 | 30.9 | 216.8 | 254.3 | 70 | 228.9 | 248.4 | |
| 5,500 | 78.6 | 229.8 | 255.2 | 5,500 | 45.3 | 216.8 | 254.3 | * | | | |
| 2,900 | 87.1 | 255.2 | 270.0 | 2,900 | 236.0 | 254.3 | 260.0 | 70 | 248.4 | 267.0 | |

** Plus 1600M BTU/hr. from propylene refrigerator
* 5 psig propylene refrigeration

TABLE II

Savings Realized by Implementation of LNG Refrigeration Relative to Conventional Plant With Ethylene/Propylene Refrigeration Basis: 500 MM lbs. $C_2H_4$/yr. Ethylene Plant Steam Credit[1] at $1.50/1000 lb.

| Example | LNF Flow Rate ($10^6$ SCFD) | % Annualized[2] Investment Savings | % Annual Operating Savings | % Annual Total Savings |
|---|---|---|---|---|
| II | 240 | 16.8 | 12.7 | 13.9 |
| III | 240 | 16.8 | 12.7 | 13.9 |
| IV | 150 | 11.8 | 14.1 | 13.4 |
| V | 236 | 13.1 | 7.6 | 9.2 |
| VI | 70 | 3.0 | 3.8 | 3.6 |

[1] Steam at 1800# and 482° C (low pressure steam taken as 87.5% of 1800# cost).
[2] Investment savings annualized at 17%.

As shown in Table II, Examples II and III yield net overall savings of 13.9% over the conventional ethylene plant of Example I, due to elimination of the ethylene and propylene refrigeration systems and operation of the forecooling recovery section at 125 psig instead of the conventional 555 psig pressure, in accordance with the present invention. With regard to investment costs for the systems in Examples II and III, the deletion of the prefractionation column in the latter Example is associated with an increased sizing requirement for the demethanizer column. The incremental investment cost for the larger demethanizer column is roughly equivalent to the investment cost of the prefractionation column, so that investment costs and savings are nearly identical in Examples II and III. Example IV embodies a scheme for using partial LNG refrigeration according to the present invention in a particularly effective manner; just enough LNG is applied for refrigeration along with some propylene refrigeration to eliminate the most costly refrigeration. Overall net savings are 13.4% over the conventional case of Example I. Example V employs total LNG refrigeration in an ethylene plant at conventional high pressure. This Example yields a net overall savings of 9.2% over Example I, a savings level which nonetheless is more than 30% less than the savings achieved by the cases (Examples II-IV) wherein the present invention is employed. Example VI represents the minimum usage of LNG which is possible for a 500 million lb./year ethylene plant operating at conventional high pressure. In this case, all of the ethylene and a portion of the propylene refrigeration is replaced by LNG. Net overall savings for Example VI are only 3.6% over Example I.

As shown above, the Examples employing the method of the instant invention are characterized by substantial cost savings over the high pressure cases of Examples V and VI. In the three Examples illustrative of the present invention, Examples II and III possess an investment cost advantage over Example IV, due to the former's complete elimination of the conventional refrigeration systems. Example IV, however, has a lower annual operating cost than Examples II and III. The reason for this difference, which is opposite to what might initially be expected based on the refrigeration systems in the two cases, concerns the refrigeration credits which are available to the conventional refrigeration system. As discussed earlier herein in connection with Example I, the propylene refrigeration credits in the conventional plant include reboiler duties for the demethanizer and $C_2$ splitter columns and prefractionation column if employed. These cooling credits are also available to the propylene refrigerant in Example IV, but are not of course available in Examples II and III.

Thus, although Examples II and III actually produce more high pressure (1800#) steam (since there are no refrigeration compressors to drive), this gain is more than offset by the low pressure steam requirements for the demethanizer column, $C_2$ splitter column and prefractionation column (in FIG. 1) reboilers. Example IV therefor achieves a higher net operating savings than Examples II and III. The overall result is that the total annual savings for Examples II and III and Example IV are comparatively close, being within 5% of one another, with Examples II and III offering the larger net savings.

Figure 10:
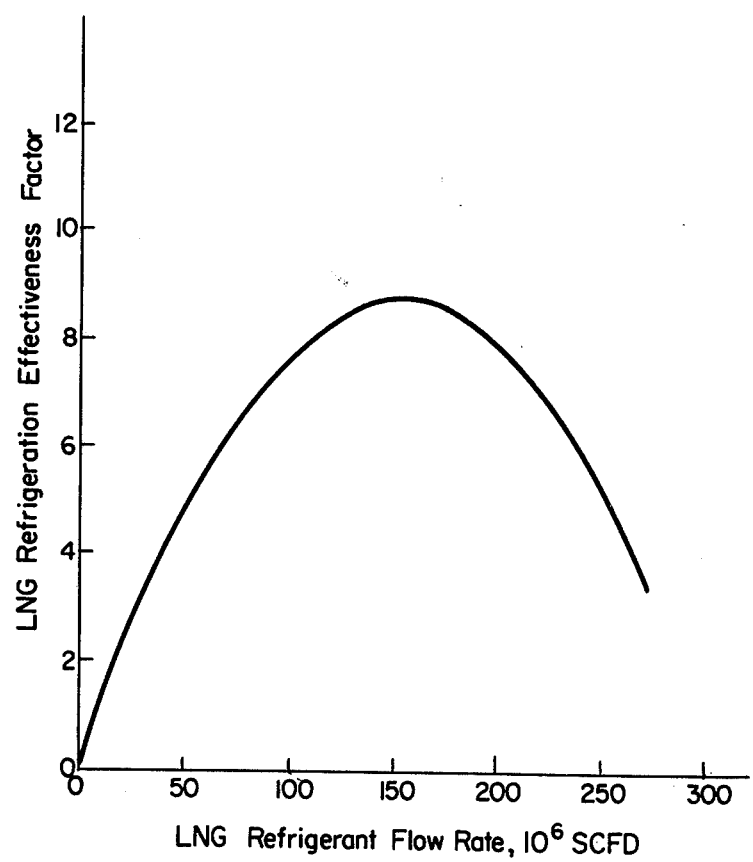
FIG. 10 is a graph of an LNG refrigeration effectiveness factor plotted against the total flow rate of LNG refrigerant heat exchanged in the ethylene plant in standard cubic feet per day, for a 500 million lbs./year ethylene plant operated in accordance with the present invention.

Based on the foregoing, a relationship between the refrigeration effectiveness and the amount of LNG applied to the ethylene plant in accordance with the present invention has been established. This relationship is shown in FIG. 10 wherein a refrigeration effectiveness factor, defined here as $$\frac{\frac{\text{unit annual savings of LNG-refrigerated plant, \$} \times 10^4}{\text{total annual cost of conventional plant, \$}}}{\text{flow rate of LNG, } 10^6 \text{ SCFD}}$$

is plotted against the LNG refrigerant flow rate in million standard cubic feet per day ($10^6$ SCFD), for a 500 million lb. ethylene/year ethylene plant operating in accordance with this invention, with LNG refrigeration being employed at least in the forecooling recovery section to condense liquid from the overhead gas recovered from the depropanizer column and in the reflux condensers of the demethanizer and $C_2$ splitter columns, with the depropanizer column and forecooling recovery section operating at low pressure below 200 psig and preferably less than 150 psig, and with the final separation section operating at higher pressure above 200 psig and preferably greater than 250 psig. As shown by FIG. 10, there is an optimum LNG usage level, when the method of this invention is employed to implement LNG refrigeration to satisfy only part of the ethylene plant's total refrigeration requirements, with the remainder being accommodated by conventional refrigeration systems. This optimum is at approximately 150 million standard cubic feet per day for a plant producing 500 million lb. ethylene and 400 million lb. propylene per year, corresponding to the embodiment of the invention illustratively described in Example IV. As used herein, the ethylene plant production rate as expressed on a per year basis is equivalent to 8280 annual operating hours.

Several quantitative criteria have been developed as guidelines for LNG refrigeration usage in accordance with the invention, relating the flow rate of LNG, in standard cubic feet per day (SCFD) to the annual rate of production of olefins (product ethylene plus product propylene) by the ethylene plant, in lbs./year. For purposes of economy with concomitant high LNG refrigeration utilization, it is generally desirable in the practice of this invention to maintain the LNG refrigeration effectiveness factor, as defined above, at a numerical value of $\geq 4$. Applied to the graph of FIG. 7, this constraint indicates that the ratio of SCFD of LNG to lbs./yr. of ethylene plus propylene products should lie between approximately 0.05 and 0.30. In the practice of the invention where an acetylene removal complex is provided, wherein LNG refrigeration is further employed in the separation of acetylene from the product ethylene stream, this ratio preferably has a value of between approximately 0.15 and 0.30.

In the illustrative examples of the invention presented herein, LNG is warmed for regasification and discharge at a pressure level of approximately 700 psig. Such pressure level provides the most efficient match of LNG to the refrigeration requirements of the ethylene plant in the specific examples considered. It will be recognized, however, that applications may be made within the scope of this invention in which LNG pressures higher or lower than those presented herein are advantageously employed.

Although preferred embodiments have been described in detail, it will be further appreciated that other embodiments are contemplated only with modification of the disclosure features, as being within the scope of the invention.

What is claimed is:

1. A process for separating a hydrocarbon feed gas mixture comprising at least $C_1$–$C_4$ constituents including ethylene to produce a separated ethylene product while simultaneously warming liquefied natural gas for regasification thereof, comprising the steps of:
   (a) providing said hydrocarbon feed gas mixture at superatmospheric pressure and fractionating same in a depropanizer column to recover overhead gas comprising $C_3$ and lighter constituents and bottoms comprising $C_4$ and heavier constituents;
   (b) cooling the overhead gas recovered from the depropanizer column to condense a liquid fraction comprising at least $C_1$–$C_2$ constituents by heat exchange with externally supplied liquefied natural gas for warming thereof, and separating said liquid fraction from the cooled overhead gas;
   (c) pressurizing the separated liquid fraction to a superatmospheric pressure higher than the pressure of said feed gas mixture;
   (d) fractionating the pressurized liquid fraction in a demethanizer column to recover a demethanizer overhead comprising methane and a demethanizer bottoms comprising at least $C_2$ constituents, and heat exchanging externally supplied liquefied natural gas with the demethanizer overhead to condense same and provide reflux for said demethanizer while warming the liquefied natural gas; and
   (e) further fractionating said demethanizer bottoms for the production of said separated ethylene product, said further fractionating including fractionation in a $C_2$ splitter column to recover ethylene as overhead product and ethane bottoms, and heat exchanging externally supplied liquefied natural gas with the $C_2$ splitter column overhead to condense same and provide reflux for said $C_2$ splitter column while warming the liquefied natural gas.

2. A process according to claim 1 wherein the condensed liquid fraction comprises $C_1$–$C_3$ constituents, said demethanizer bottoms comprises $C_2$–$C_3$ constituents, and said further fractionating of step (e) includes fractionating said demethanizer bottoms in a deethanizer column to recover a $C_2$ overhead and $C_3$ bottoms and fractionating said $C_2$ overhead in said $C_2$ splitter column.

3. A process according to claim 1 wherein said hydrocarbon feed gas mixture is provided at a first superatmospheric pressure and the overhead gas recovered from the depropanizer column is cooled in step (b) to condense a first liquid fraction comprising $C_1$–$C_3$ constituents, comprising the further steps of:

pressurizing said first liquid fraction to a second higher-than-first superatmospheric pressure;

fractionating the pressurized first liquid fraction in a prefractionation column to recover a prefractionated overhead comprising $C_2$ and lighter constituents and a prefractionated bottoms comprising $C_2$–$C_3$ constituents;

fractionating said prefractionated bottoms in a deethanizer column to recover a $C_2$ overhead and $C_3$ bottoms;

further cooling the uncondensed overhead gas from which the first liquid fraction has been separated to condense a second liquid fraction comprising $C_1$–$C_2$ constituents by heat exchange with externally supplied liquefied natural gas for warming thereof, and separating said second liquid fraction from the further cooled gas as the separated liquid fraction of step (b);

wherein said second liquid fraction is pressurized to a third higher-than-first superatmospheric pressure in the pressurizing of step (c), said prefractionated overhead recovered from said prefractionation column is fractionated in said demethanizer column with said pressurized second liquid fraction in the fractionating of step (d), and said $C_2$ overhead recovered from said deethanizer column and said demethanizer bottoms are fractionated in said $C_2$ splitter column in the further fractionating in step (e).

4. A process according to claim 1 wherein said hydrocarbon feed gas mixture is provided at a first superatmospheric pressure and the overhead gas recovered from the depropanizer column is cooled in step (b) to condense a first liquid fraction comprising $C_1$–$C_3$ constituents, comprising the further steps of:

pressurizing said first liquid fraction to a second higher-than-first superatmospheric pressure;

fractionating the pressurized first liquid fraction in a deethanizer column to recover a $C_1$–$C_2$ overhead and $C_3$ bottoms;

further cooling the uncondensed overhead gas from which the first liquid fraction has been separated to condense a second liquid fraction comprising $C_1$–$C_2$ constituents by heat exchange with externally supplied liquefied natural gas for warming thereof, and separating said second liquid fraction from the further cooled gas as the separated liquid fraction of step (b);

wherein said second liquid fraction is pressurized to a third higher-than-first superatmospheric pressure in the pressurizing of step (c), said $C_1$–$C_2$ overhead recovered from said deethanizer column is fractionated in said demethanizer column with said pressurized second liquid fraction in said fractionating of step (d), and said demethanizer bottoms are fractionated in said $C_2$ splitter column in the further fractionating in step (e).

5. A process according to claim 1 wherein said superatmospheric pressure of said feed gas mixture in step (a) is less than 200 psig and the superatmospheric pressure of the pressurized liquid fraction in step (c) is greater than 200 psig.

6. A process according to claim 1 wherein the hydrocarbon feed gas mixture contains propylene comprising fractionation in a deethanizer column to recover a $C_3$ bottoms containing propylene and fractionating said $C_3$ bottoms in a $C_3$ splitter column to recover propylene as overhead product, wherein said superatmospheric pressure of said feed gas mixture is less than 150 psig and the superatmospheric pressure of the pressurized liquid fraction in step (c) is greater than 250 psig, and the ratio of the total flow rate of liquefied natural gas heat exchanged in said process as refrigerant in standard cubic feet per day to the rate of production of olefins by said process in lbs/year is between 0.05 and 0.30.

7. A process according to claim 1 wherein ethylene overhead product from said $C_2$ splitter column containing acetylene is treated to remove substantially all acetylene therefrom, by the steps of:
  (a) contacting ethylene overhead product and externally supplied acetone in an absorber column and absorbing acetylene in said acetone therein to recover overhead final product of substantially pure ethylene and bottoms liquid comprising acetone and acetylene;
  (b) cooling the bottoms liquid recovered from the absorber column by heat exchange with externally supplied liquefied natural gas for warming thereof;
  (c) fractionating the cooled absorber column bottoms liquid in a first fractionation column to recover overhead containing a lower fraction of acetylene and bottoms containing a higher fraction of acetylene, heat exchanging externally supplied liquefied natural gas with the first fractionation column overhead to condense same and provide reflux for said first fractionation column while warming the liquefied natural gas, and returning the first fractionation column overhead to the absorber column as recycle therefor;
  (d) fractionating said first fractionation column bottoms in a second fractionation column to recover acetone bottoms and overhead gas containing acetylene, heat exchanging externally supplied liquefied natural gas with the acetone bottoms recovered from said second fractionation column for cooling thereof while warming the liquefied natural gas, and returning cooled acetone bottoms from said second fractionation column to said absorber column as the acetone feed therefor; and
  (e) cooling the acetylene-containing overhead gas recovered from said second fractionation column to condense substantially all acetone therein by heat exchange with externally supplied liquefied natural gas for warming thereof, separating condensate from the cooled overhead gas and returning said condensate to said second fractionation column as recycle therefor, and discharging cooled overhead gas as substantially pure acetylene.

8. A process according to claim 7 wherein externally supplied liquefied natural gas is heat exchanged with the overhead of said absorber column to condense same and provide reflux for said absorber column while warming the liquefied natural gas.

9. A process according to claim 7 wherein the ratio of the total flow rate of liquefied natural gas heat exchanged in said process as refrigerant in standard cubic ft. per day to the rate of production of olefins by said process in lbs./year is between 0.15 and 0.30.

10. A process for separating a hydrocarbon feed gas mixture comprising at least $C_1$-$C_4$ constituents including ethylene to produce a separated ethylene product while simultaneously warming liquefied natural gas for regasification thereof, comprising the steps of:
  (a) providing said hydrocarbon feed gas mixture at superatmospheric pressure and fractionating same in a depropanizer column to recover overhead gas comprising $C_3$ and lighter constituents and bottoms comprising $C_4$ and heavier constituents;
  (b) cooling the overhead gas recovered from the depropanizer column to condense a liquid fraction comprising $C_1$-$C_3$ constituents by heat exchange with externally supplied liquefied natural gas for warming thereof, and separating the liquid fraction from the cooled gas;
  (c) pressurizing the separated liquid fraction to a superatmospheric pressure higher than the pressure of said feed gas mixture;
  (d) fractionating the pressurized liquid fraction in a demethanizer column to recover a demethanizer overhead comprising methane and a demethanizer bottoms comprising $C_2$-$C_3$ constituents, and heat exchanging externally supplied liquefied natural gas with the demethanizer overhead to condense same and provide reflux for said demethanizer while warming the liquefied natural gas;
  (e) fractionating said demethanizer bottoms in a deethanizer column to recover a $C_2$ overhead and $C_3$ bottoms; and
  (f) fractionating said $C_2$ overhead in a $C_2$ splitter column to recover ethylene as overhead product and ethane bottoms, and heat exchanging externally supplied liquefied natural gas with the $C_2$ splitter column overhead to condense same and provide reflux for said $C_2$ splitter column while warming the liquefied natural gas.

11. A process for separating a hydrocarbon feed gas mixture comprising at least $C_1$-$C_4$ constituents including ethylene to produce a separated ethylene product while simultaneously warming liquefied natural gas for regasification thereof, comprising the steps of:
  (a) providing said hydrocarbon feed gas mixture at a first superatmospheric pressure and fractionating same in a depropanizer column to recover overhead gas comprising $C_3$ and lighter constituents and bottoms comprising $C_4$ and heavier constituents;
  (b) cooling the overhead gas recovered from the depropanizer column to condense a first liquid fraction comprising $C_1$-$C_3$ constituents by heat exchange with externally supplied liquefied natural gas for warming thereof, and separating said first liquid fraction from the cooled overhead gas;
  (c) pressurizing said first liquid fraction to a second higher-than-first superatmospheric pressure;
  (d) fractionating the pressurized first liquid fraction in a deethanizer column to recover $C_1$-$C_2$ overhead and a $C_3$ bottoms;
  (e) further cooling the uncondensed overhead gas from step (b) to condense a second liquid fraction comprising $C_1$-$C_2$ constituents by heat exchange with externally supplied liquefied natural gas for warming thereof, and separating said second liquid fraction from the further cooled gas;
  (f) pressurizing said second liquid fraction to a third higher-than-first superatmospheric pressure;
  (g) fractionating the pressurized second liquid fraction and said $C_1$-$C_2$ overhead of step (d) in a demethanizer column to recover a demethanizer overhead comprising methane and a demethanizer bottoms comprising $C_2$ constituents, and heat exchanging externally supplied liquefied natural gas with the demethanizer overhead to condense same and provide reflux for said demethanizer while warming the liquefied natural gas; and
  (h) fractionating said demethanizer bottoms in a $C_2$ splitter column to recover ethylene as overhead product and ethane bottoms, and heat exchanging externally supplied liquefied natural gas with the $C_2$ splitter column overhead to condense same and provide reflux for said $C_2$ splitter column while warming the liquefied natural gas.

12. A process for separating a hydrocarbon feed gas mixture comprising at least $C_1$–$C_4$ constituents including ethylene to produce a separated ethylene product while simultaneously warming liquefied natural gas for regasification thereof, comprising the steps of:
   (a) providing said hydrocarbon feed gas mixture at a first superatmospheric pressure and fractionating same in a depropanizer column to recover overhead gas comprising $C_3$ and lighter constituents and bottoms comprising $C_4$ and heavier constituents;
   (b) cooling the overhead gas recovered from the depropanizer column to condense a first liquid fraction comprising $C_1$–$C_3$ constituents by heat exchange with externally supplied liquefied natural gas for warming thereof, and separating said first liquid fraction from the cooled overhead gas;
   (c) pressurizing said first liquid fraction to a second higher-than-first superatmospheric pressure;
   (d) fractionating the pressurized first liquid fraction in a prefractionation column to recover a prefractionated overhead comprising $C_2$ and lighter constituents and a prefractionated bottoms comprising $C_2$–$C_3$ constituents;
   (e) further cooling the uncondensed overhead gas from step (b) to condense a second liquid fraction comprising $C_1$–$C_2$ constituents by heat exchange with externally supplied liquefied natural gas for warming thereof, and separating said second liquid fraction from the further cooled gas;
   (f) pressurizing said second liquid fraction to a third higher-than-first superatmospheric pressure;
   (g) fractionating the pressurized second liquid fraction and said prefractionated overhead of step (d) in a demethanizer column to recover a demethanizer overhead comprising methane and a demethanizer bottoms comprising $C_2$ constituents, and heat exchanging externally supplied liquefied natural gas with the demethanizer overhead to condense same and provide reflux for said demethanizer while warming the liquefied natural gas;
   (h) fractionating said prefractionated bottoms from step (d) in a deethanizer column to recover a $C_2$ overhead and $C_3$ bottoms; and
   (i) fractionating said $C_2$ overhead and said demethanizer bottoms in a $C_2$ splitter column to recover ethylene as overhead product and ethane bottoms, and heat exchanging externally supplied liquefied natural gas with the $C_2$ splitter column overhead to condense same and provide reflux for said $C_2$ splitter column while warming the liquefied natural gas.

13. A process according to claim 12 wherein externally supplied liquefied natural gas is heat exchanged with the overhead of said depropanizer, deethanizer and prefractionation columns to condense same and provide reflux for said columns while warming the liquefied natural gas.

14. A process according to claim 12 wherein said first superatmospheric pressure of step (a) is less than 200 psig, and said second superatmospheric pressure of step (c) and said third superatmospheric pressure of step (f) are greater than 200 psig.

15. A process according to claim 12 wherein said hydrocarbon feed gas mixture contains propylene comprising fractionating said deethanizer bottoms in a $C_3$ splitter column to recover propylene as overhead product.

16. A process according to claim 12 wherein said first superatmospheric pressure of step (a) is less than 150 psig and said second superatmospheric pressure of step (c) and said third superatmospheric pressure of step (f) are greater than 250 psig.

17. A process according to claim 12 wherein the ratio of the total flow rate of liquefied natural gas heat exchanged in said process as refrigerant in standard cubic ft. per day to the rate of production of olefins by said process in lbs./year is between 0.05 and 0.30.

18. A process for separating a hydrocarbon feed gas mixture comprising at least $C_1$–$C_4$ constituents including acetylene, propylene and ethylene to produce a separated ethylene product while simultaneously warming liquefied natural gas for regasification thereof, comprising the steps of:
   (a) providing said hydrocarbon feed gas mixture at superatmospheric pressure below 200 psig and fractionating same in a depropanizer column to recover overhead gas comprising $C_3$ and lighter constituents and bottoms comprising $C_4$ and heavier constituents;
   (b) cooling the overhead gas recovered from the depropanizer column to condense a first liquid fraction comprising $C_1$–$C_3$ constituents by heat exchange with externally supplied liquefied natural gas for warming thereof, and separating said first liquid fraction from the cooled overhead gas;
   (c) pressurizing said first liquid fraction to a superatmospheric pressure greater than 200 psig;
   (d) fractionating the pressurized first liquid fraction in a prefractionation column to recover a prefractionated overhead comprising $C_2$ and lighter constituents and a prefractionated bottoms comprising $C_2$–$C_3$ constituents;
   (e) further cooling the uncondensed overhead gas from step (b) to condense a second liquid fraction comprising $C_1$–$C_2$ constituents by heat exchange with externally supplied liquefied natural gas for warming thereof, and separating said second liquid fraction from the further cooled gas;
   (f) pressurizing said second liquid fraction to a superatmospheric pressure greater than 200 psig;
   (g) fractionating the pressurized second liquid fraction and said prefractionated overhead of step (d) in a demethanizer column to recover a demethanizer overhead comprising methane and a demethanizer bottoms comprising $C_2$ constituents, and heat exchanging externally supplied liquefied natural gas with the demethanizer overhead to condense same and provide reflux for said demethanizer column while warming the liquefied natural gas;
   (h) fractionating said prefractionated bottoms from step (d) in a deethanizer to recover a $C_2$ overhead and $C_3$ bottoms;
   (i) fractionating said $C_2$ overhead and said demethanizer bottoms in a $C_2$ splitter column to recover ethylene as overhead product containing acetylene and ethane bottoms, and heat exchanging externally supplied liquefied natural gas with the $C_2$ splitter column overhead to condense same and provide reflux for said $C_2$ splitter column while warming the liquefied natural gas;

(j) fractionating said deethanizer bottoms in a C$_3$ splitter column to recover propylene as overhead product;

(k) contacting ethylene overhead product from said C$_2$ splitter column and externally supplied acetone into an absorber column and absorbing acetylene in said acetone therein to recover overhead final product of substantially pure ethylene and bottoms liquid comprising acetone and acetylene;

(l) cooling the bottoms liquid recovered from the absorber column by heat exchange with externally supplied liquefied natural gas for warming thereof;

(m) fractionating the cooled absorber column bottoms liquid in a first fractionation column to recover overhead containing a lower fraction of acetylene and bottoms containing a higher fraction of acetylene, heat exchanging externally supplied liquefied natural gas with the first fractionation column overhead to condense same and provide reflux for said first fractionation column while warming the liquefied natural gas, and returning the first fractionation column overhead to the absorber column as recycle therefor;

(n) fractionating said first fractionation column bottoms in a second fractionation column to recover acetone bottoms and overhead gas containing acetylene, heat exchanging externally supplied liquefied natural gas with the acetone bottoms recovered from said second fractionation column for cooling thereof while warming the liquefied natural gas, and returning a first part of the cooled acetone bottoms from said second fractionation column to said absorber column as the acetone feed therefor, and a second part thereof to said first fractionation column as recycle therefor; and (o) cooling the acetylene-containing overhead gas recovered from said second fractionation column to condense substantially all acetone therein by heat exchange with externally supplied liquefied natural gas for warming thereof, separating condensate from the cooled overhead gas and returning said condensate to said fractionation column as recycle therefor, and discharging the cooled overhead gas as substantially pure acetylene, said process being characterized by a ratio of the total flow rate of liquefied natural gas heat exchanged in said process as refrigerant in standard cubic feet per day to the rate of production of olefins by said process in lbs./year of between 0.05 and 0.30.

19. A process according to claim 18 wherein externally supplied liquefied natural gas is heat exchanged with the overhead of said depropanizer, prefractionation, deethanizer and absorber columns to condense same and provide reflux for said columns while warming the liquefied natural gas.

20. A process according to claim 18 wherein the ratio of the total flow rate of liquefied natural gas heat exchanged in said process as refrigerant in standard cubic feet per day to the rate of production of olefins by said process in lbs./year is between 0.15 and 0.30.

* * * * *